US 9,988,659 B1

United States Patent
Benner et al.

(10) Patent No.: US 9,988,659 B1
(45) Date of Patent: Jun. 5, 2018

(54) IN VIVO CONVERSION OF NUCLEOSIDES IN PLASMID DNA

(71) Applicants: Steven A Benner, Gainesville, FL (US); Ryan Shaw, Gainesville, FL (US)

(72) Inventors: Steven A Benner, Gainesville, FL (US); Ryan Shaw, Gainesville, FL (US)

( * ) Notice: Subject to any disclaimer, the term of this patent is extended or adjusted under 35 U.S.C. 154(b) by 346 days.

(21) Appl. No.: 14/218,405

(22) Filed: Mar. 18, 2014

Related U.S. Application Data

(63) Continuation of application No. 12/653,613, filed on Dec. 16, 2009, now Pat. No. 9,334,534.

(60) Provisional application No. 61/802,913, filed on Mar. 18, 2013.

(51) Int. Cl.
   C12P 19/34 (2006.01)

(52) U.S. Cl.
   CPC .................................. C12P 19/34 (2013.01)

(58) Field of Classification Search
   USPC ........................ 435/6.1, 6.12, 91.1
   See application file for complete search history.

(56) References Cited

U.S. PATENT DOCUMENTS

| | | |
|---|---|---|
| 5,432,272 A | 7/1995 | Benner |
| 5,965,364 A | 10/1999 | Benner |
| 6,001,983 A | 12/1999 | Benner |
| 6,037,120 A | 3/2000 | Benner |
| 6,140,496 A | 10/2000 | Benner |
| 6,617,106 B1 | 9/2003 | Benner |
| 6,627,456 B1 | 9/2003 | Benner |

*Primary Examiner* — Jezia Riley

(57) ABSTRACT

The instant invention provides for the assembly of large DNA oligonucleotide constructs by the self-assembly of multiple oligonucleotide fragments, wherein the assembly is guided by the hybridization between non-standard nucleotides that form non-standard nucleobase pairs orthogonal to the standard T:A and C:G nucleobase pairs. Adding nucleobase pairs increases the information density of the fragments, minimizing off-target hybridization. The invention further provides rules and methods for converting non-standard pairs into standard pairs using polymerase copying with conversion.

4 Claims, 10 Drawing Sheets

```
                         SEQUENCE LISTING

<160> NUMBER OF SEQ ID NOS: 140

<210> SEQ ID NO 1
  <211> LENGTH: 44
  <212> TYPE: DNA
  <213> ORGANISM: Artificial Sequence
  <220> FEATURE:
  <223> OTHER INFORMATION: Synthetic
  <220> FEATURE:
  <221> NAME/KEY: misc_feature
  <222> LOCATION: (1)..(1)
  <223> OTHER INFORMATION: 2-amino-8-(1'-beta-D-2'-deoxyribofuranosyl)-
        imidazo[1,2-a]-1,3,5-tiazin-4(8H)one

<400> SEQUENCE: 1
ncatgtctga tcctgcactg ctgggcsctt gactctcgta cctg                   44

<210> SEQ ID NO 2
  <211> LENGTH: 43
  <212> TYPE: DNA
  <213> ORGANISM: Artificial Sequence
  <220> FEATURE:
  <223> OTHER INFORMATION: Synthetic
  <220> FEATURE:
  <221> NAME/KEY: misc_feature
  <222> LOCATION: (1)..(1)
  <223> OTHER INFORMATION: 2-amino-8-(1'-beta-D-2'-deoxyribofuranosyl)-
        imidazo[1,2-a]-1,3,5-triazin-4(8H)one

<400> SEQUENCE: 2
ngctcaggta cgagagtcaa gggcccagca gtgcaggatc aga                    43

<210> SEQ ID NO 3
  <211> LENGTH: 40
  <212> TYPE: DNA
  <213> ORGANISM: Artificial Sequence
  <220> FEATURE:
  <223> OTHER INFORMATION: Synthetic
  <220> FEATURE:
  <221> NAME/KEY: misc_feature
  <222> LOCATION: (1)..(1)
  <223> OTHER INFORMATION: 2-amino-8-(1'-beta-D-2'-deoxyribofuranosyl)-
        imidazo[1,2-a]-1,3,5-triazin-4(8H)one
  <220> FEATURE:
  <221> NAME/KEY: misc_feature
  <222> LOCATION: (1)..(1)
  <223> OTHER INFORMATION: 2-amino-8-(1'-beta-D-2'-deoxyribofuranosyl)-
        imidazo[1,2-a]-1,3,5-triazin-4(8H)one
  <220> FEATURE:
  <221> NAME/KEY: misc_feature
  <222> LOCATION: (1)..(1)
  <223> OTHER INFORMATION: 2-amino-8-(1'-beta-D-2'-deoxyribofuranosyl)-
        imidazo[1,2-a]-1,3,5-triazin-4(8H)one
  <220> FEATURE:
  <221> NAME/KEY: misc_feature
  <222> LOCATION: (1)..(1)
  <223> OTHER INFORMATION: 2-amino-8-(1'-beta-D-2'-deoxyribofuranosyl)-
        imidazo[1,2-a]-1,3,5-triazin-4(8H)one

<400> SEQUENCE: 3
ncatgtcaac tcctgcgtgc ggccttgact ctcgtacctg                        40

<210> SEQ ID NO 4
  <211> LENGTH: 39
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (1)..(1)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (1)..(1)
<223> OTHER INFORMATION: 2-amino-8-(1'-beta-D-2'-deoxyribofuranosyl)-
      imidazo[1,2-a]-1,3,5-triazin-4(8H)one

<400> SEQUENCE: 4
ngctcaggta cgagagtcaa ggccgcacgc aggagttga                              39

<210> SEQ ID NO 5
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (10)..(10)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (17)..(17)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (19)..(19)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (20)..(20)
<223> OTHER INFORMATION: 6-amino-5-nitro-3-(1'-beta-D-2'-
      deoxyribofuranosyl)-2(1H)-pyridone

<400> SEQUENCE: 5
ncatgtcaan tcctgcntnn ggccttgact ctcgtacctg                             40

<210> SEQ ID NO 6
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (25)..(25)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
```

```
<221> NAME/KEY: misc_feature
<222> LOCATION: (26)..(26)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (28)..(28)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (35)..(35)
<223> OTHER INFORMATION: 2-amino-8-(1'-beta-D-2'-deoxyribofuranosyl)-
      imidazo[1,2-a]-1,3,5-triazin-4(8H)one

<400> SEQUENCE: 6
ngctcaggta cgagagtcaa ggccnnangc agganttga                                39

<210> SEQ ID NO 7
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (10)..(10)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (12)..(13)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (15)..(15)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (16)..(16)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (17)..(17)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (19)..(19)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (20)..(20)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (21)..(22)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (23)..(24)
<223> OTHER INFORMATION: 6-amino-5-nitro-3-(1'-beta-D-2'-
      deoxyribofuranosyl)-2(1H)-pyridone

<400> SEQUENCE: 7
```
ncatgtcaan tnntnnntnn nnnnttgact ctcgtacctg         40

<210> SEQ ID NO 8
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (21)..(22)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (23)..(24)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (25)..(25)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (26)..(26)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (28)..(28)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (29)..(29)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (30)..(30)
<223> OTHER INFORMATION: n =
      6-amino-5-nitro-3-(1'-beta-D-2'-deoxyribofuranosyl)-2(1H)-pyridon
      e
<220> FEATURE:
<221> NAME/KEY: misc_feature
<222> LOCATION: (32)..(32)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (33)..(33)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (35)..(35)
<223> OTHER INFORMATION: 2-amino-8-(1'-beta-D-2'-deoxyribofuranosyl)-
      imidazo[1,2-a]-1,3,5-triazin-4(8H)one

<400> SEQUENCE: 8
ngctcaggta cgagagtcaa nnnnnnannn annanttga         39

<210> SEQ ID NO 9
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature

```
<222> LOCATION: (7)..(8)
<223> OTHER INFORMATION: 2-amino-8-(1'-beta-D-2'-deoxyribofuranosyl)-
      imidazo[1,2-a]-1,3,5-triazin-4(8H)one

<400> SEQUENCE: 9
agtcaanngc ccagcagtgc aggatcagac atgtcctgaa ccgacgaccg ggtcgaattt     60

<210> SEQ ID NO 10
<211> LENGTH: 60
<212> TYPE: DNA
<213> ORGANISM: Artificial Sequence
<220> FEATURE:
<223> OTHER INFORMATION: Synthetic

<400> SEQUENCE: 10
agtcaagggc ccagcagtgc aggatcagac atgtcctgaa ccgacgaccg ggtcgaattt     60

<210> SEQ ID NO 11
<211> LENGTH: 60
<212> TYPE: DNA
<213> ORGANISM: Artificial Sequence
<220> FEATURE:
<223> OTHER INFORMATION: Synthetic

<400> SEQUENCE: 11
agtcaaaggc ccagcagtgc aggatcagac atgtcctgaa ccgacgaccg ggtcgaattt     60

<210> SEQ ID NO 12
<211> LENGTH: 59
<212> TYPE: DNA
<213> ORGANISM: Artificial Sequence
<220> FEATURE:
<223> OTHER INFORMATION: Synthetic

<400> SEQUENCE: 12
agtaaaggcc cagcagtgca ggatcagaca tgtcctgaac cgacgaccgg gtcgaattt      59

<210> SEQ ID NO 13
<211> LENGTH: 60
<212> TYPE: DNA
<213> ORGANISM: Artificial Sequence
<220> FEATURE:
<223> OTHER INFORMATION: Synthetic

<400> SEQUENCE: 13
agtcaagggc ccagcagtgc aggatcagac atgtcctgaa ccgacgaccg ggtcgaattt     60

<210> SEQ ID NO 14
<211> LENGTH: 60
<212> TYPE: DNA
<213> ORGANISM: Artificial Sequence
<220> FEATURE:
<223> OTHER INFORMATION: Synthetic

<400> SEQUENCE: 14
agtcaagggc ccagcagtgc aggatcagac atgtcctgaa ccgacgaccg ggtcgaattt     60

<210> SEQ ID NO 15
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: 2-amino-8-(1'-beta-D-2'-deoxyribofuranosyl)-
``` imidazo[1,2-a]-1,3,5-tiazin-4(8H)one
<220> FEATURE:
<221> NAME/KEY: misc_feature
<222> LOCATION: (19)..(19)
<223> OTHER INFORMATION: 6-amino-5-nitro-3-(1'-beta-D-2'-
      deoxyribofuranosyl)-2(1H)-pyridone

<400> SEQUENCE: 15
catgtcaact cctgcgtnng gccttgactc tcgtacct                         38

<210> SEQ ID NO 16
<211> LENGTH: 60
<212> TYPE: DNA
<213> ORGANISM: Artificial Sequence
<220> FEATURE:
<223> OTHER INFORMATION: Synthetic

<400> SEQUENCE: 16
cgacccggtc gtcggttcag gacatgtcaa ctcctgcgtg cggccttgac tctcgtacct  60

<210> SEQ ID NO 17
<211> LENGTH: 60
<212> TYPE: DNA
<213> ORGANISM: Artificial Sequence
<220> FEATURE:
<223> OTHER INFORMATION: Synthetic

<400> SEQUENCE: 17
cgacccggtc gtcggttcag gacatgtcaa ctcctgcgta cggccttgac tctcgtacct  60

<210> SEQ ID NO 18
<211> LENGTH: 60
<212> TYPE: DNA
<213> ORGANISM: Artificial Sequence
<220> FEATURE:
<223> OTHER INFORMATION: Synthetic

<400> SEQUENCE: 18
cgacccggtc gtcggttcag gacatgtcaa ctcctgcgta cggccttgac tctcgtacct  60

<210> SEQ ID NO 19
<211> LENGTH: 60
<212> TYPE: DNA
<213> ORGANISM: Artificial Sequence
<220> FEATURE:
<223> OTHER INFORMATION: Synthetic

<400> SEQUENCE: 19
cgacccggtc gtcggttcag gacatgtcaa ctcctgcgta cggccttgac tctcgtacct  60

<210> SEQ ID NO 20
<211> LENGTH: 60
<212> TYPE: DNA
<213> ORGANISM: Artificial Sequence
<220> FEATURE:
<223> OTHER INFORMATION: Synthetic

<400> SEQUENCE: 20
cgacccggtc gtcggttcag gacatgtcaa ctcctgcgta cggccttgac tctcgtacct  60

<210> SEQ ID NO 21
<211> LENGTH: 60
<212> TYPE: DNA
<213> ORGANISM: Artificial Sequence
<220> FEATURE:
<223> OTHER INFORMATION: Synthetic

<400> SEQUENCE: 21
cgacccggtc gtcggttcag gacatgtcaa ctcctgcgta cggccttgac tctcgtacct    60

<210> SEQ ID NO 22
<211> LENGTH: 60
<212> TYPE: DNA
<213> ORGANISM: Artificial Sequence
<220> FEATURE:
<223> OTHER INFORMATION: Synthetic

<400> SEQUENCE: 22
cgacccggtc gtcggttcag gacatgtcaa ctcctgcgtg tggccttgac tctcgtacct    60

<210> SEQ ID NO 23
<211> LENGTH: 59
<212> TYPE: DNA
<213> ORGANISM: Artificial Sequence
<220> FEATURE:
<223> OTHER INFORMATION: Synthetic

<400> SEQUENCE: 23
cgacccggtc gtcggttcag gacatgtcaa ctcctgcgta cggccttgac tctcgtacc     59

<210> SEQ ID NO 24
<211> LENGTH: 60
<212> TYPE: DNA
<213> ORGANISM: Artificial Sequence
<220> FEATURE:
<223> OTHER INFORMATION: Synthetic

<400> SEQUENCE: 24
cgacccggtc gtcggttcag gacatgtcaa ctcctgcgtg tggccttgac tctcgtacct    60

<210> SEQ ID NO 25
<211> LENGTH: 60
<212> TYPE: DNA
<213> ORGANISM: Artificial Sequence
<220> FEATURE:
<223> OTHER INFORMATION: Synthetic

<400> SEQUENCE: 25
cgacccggtc gtcggttcag gacatgtcaa ctcctgcgta cggccttgac tctcgtacct    60

<210> SEQ ID NO 26
<211> LENGTH: 60
<212> TYPE: DNA
<213> ORGANISM: Artificial Sequence
<220> FEATURE:
<223> OTHER INFORMATION: Synthetic

<400> SEQUENCE: 26
cgacccggtc gtcggttcag gacatgtcaa ctcctgcgta cggccttgac tctcgtacct    60

<210> SEQ ID NO 27
<211> LENGTH: 60
<212> TYPE: DNA
<213> ORGANISM: Artificial Sequence
<220> FEATURE:
<223> OTHER INFORMATION: Synthetic

<400> SEQUENCE: 27
cgacccggtc gtcggttcag gacatgtcaa ctcctgcgta cggccttgac tctcgtacct    60

<210> SEQ ID NO 28
<211> LENGTH: 60

```
<212> TYPE: DNA
<213> ORGANISM: Artificial Sequence
<220> FEATURE:
<223> OTHER INFORMATION: Synthetic

<400> SEQUENCE: 28
cgacccggtc gtcggttcag gacatgtcaa ctcctgcgta cggccttgac tctcgtacct    60

<210> SEQ ID NO 29
<211> LENGTH: 60
<212> TYPE: DNA
<213> ORGANISM: Artificial Sequence
<220> FEATURE:
<223> OTHER INFORMATION: Synthetic

<400> SEQUENCE: 29
cgacccggtc gtcggttcag gacatgtcaa ctcctgcgta cggccttgac tctcgtacct    60

<210> SEQ ID NO 30
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (18)..(18)
<223> OTHER INFORMATION: 2-amino-8-(1'-beta-D-2'-deoxyribofuranosyl)-
      imidazo[1,2-a]-1,3,5-triazin-4(8H)one

<400> SEQUENCE: 30
catgtcaact cctgcntncg gccttgactc tcgtacct    38

<210> SEQ ID NO 31
<211> LENGTH: 60
<212> TYPE: DNA
<213> ORGANISM: Artificial Sequence
<220> FEATURE:
<223> OTHER INFORMATION: Synthetic

<400> SEQUENCE: 31
cgacccggtc gtcggttcag gacatgtcaa ctcctgcgtg cggccttgac tctcgtacct    60

<210> SEQ ID NO 32
<211> LENGTH: 60
<212> TYPE: DNA
<213> ORGANISM: Artificial Sequence
<220> FEATURE:
<223> OTHER INFORMATION: Synthetic

<400> SEQUENCE: 32
cgacccggtc gtcggttcag gacatgtcaa ctcctgcgtg cggccttgac tctcgtacct    60

<210> SEQ ID NO 33
<211> LENGTH: 60
<212> TYPE: DNA
<213> ORGANISM: Artificial Sequence
<220> FEATURE:
<223> OTHER INFORMATION: Synthetic

<400> SEQUENCE: 33
cgacccggtc gtcggttcag gacatatcaa ctcctgcgtg cggccttgac tctcgtacct    60
```

<210> SEQ ID NO 34
<211> LENGTH: 60
<212> TYPE: DNA
<213> ORGANISM: Artificial Sequence
<220> FEATURE:
<223> OTHER INFORMATION: Synthetic

<400> SEQUENCE: 34
cgacccggtc gtcggttcag gacatgtcaa ctcctgcgtg cggccttgac tctcgtacct    60

<210> SEQ ID NO 35
<211> LENGTH: 60
<212> TYPE: DNA
<213> ORGANISM: Artificial Sequence
<220> FEATURE:
<223> OTHER INFORMATION: Synthetic

<400> SEQUENCE: 35
cgactcggtc gtcggttcag gacatgtcaa ctcctgcgtg cggccttgac tctcgtacct    60

<210> SEQ ID NO 36
<211> LENGTH: 60
<212> TYPE: DNA
<213> ORGANISM: Artificial Sequence
<220> FEATURE:
<223> OTHER INFORMATION: Synthetic

<400> SEQUENCE: 36
cgacccggtc gtcggttcag gacatgtcaa ctcctgcgtg cggccttgac tctcgtacct    60

<210> SEQ ID NO 37
<211> LENGTH: 60
<212> TYPE: DNA
<213> ORGANISM: Artificial Sequence
<220> FEATURE:
<223> OTHER INFORMATION: Synthetic

<400> SEQUENCE: 37
cgacccggtc gtcggttcag gacatgtcaa ctcctgcgtg cggccttgac tctcgtacct    60

<210> SEQ ID NO 38
<211> LENGTH: 60
<212> TYPE: DNA
<213> ORGANISM: Artificial Sequence
<220> FEATURE:
<223> OTHER INFORMATION: Synthetic

<400> SEQUENCE: 38
cgacccggtc gtcggttcag gacatgtcaa ctcctgcgtg cggccttgac tctcgtacct    60

<210> SEQ ID NO 39
<211> LENGTH: 60
<212> TYPE: DNA
<213> ORGANISM: Artificial Sequence
<220> FEATURE:
<223> OTHER INFORMATION: Synthetic

<400> SEQUENCE: 39
cgacccggtc gtcggttcag gacatgtcaa ctcctgcgtg cggccttgac tctcgtacct    60

<210> SEQ ID NO 40
<211> LENGTH: 60
<212> TYPE: DNA
<213> ORGANISM: Artificial Sequence
<220> FEATURE:
<223> OTHER INFORMATION: Synthetic -continued

<400> SEQUENCE: 40
cgacccggtc gtcggttcag gacatgtcaa ctcctgcgtg cggccttgac tctcgtacct    60

<210> SEQ ID NO 41
<211> LENGTH: 60
<212> TYPE: DNA
<213> ORGANISM: Artificial Sequence
<220> FEATURE:
<223> OTHER INFORMATION: Synthetic

<400> SEQUENCE: 41
cgacccggtc gtcggttcag gacatgtcaa ctcctgcgtg cggccttgac tctcgtacct    60

<210> SEQ ID NO 42
<211> LENGTH: 60
<212> TYPE: DNA
<213> ORGANISM: Artificial Sequence
<220> FEATURE:
<223> OTHER INFORMATION: Synthetic

<400> SEQUENCE: 42
cgacccggtc gtcggttcag gacatgtcaa ctcctgcgtg cggccttgac tctcgtacct    60

<210> SEQ ID NO 43
<211> LENGTH: 60
<212> TYPE: DNA
<213> ORGANISM: Artificial Sequence
<220> FEATURE:
<223> OTHER INFORMATION: Synthetic

<400> SEQUENCE: 43
cgacccggtc gtcggttcag gacatgtcaa ctcctgcgtg cggccttgac tctcgtacct    60

<210> SEQ ID NO 44
<211> LENGTH: 60
<212> TYPE: DNA
<213> ORGANISM: Artificial Sequence
<220> FEATURE:
<223> OTHER INFORMATION: Synthetic

<400> SEQUENCE: 44
cgacccggtc gtcggttcag gacatgtcaa ctcctgcgtg cggccttgac tctcgtacct    60

<210> SEQ ID NO 45
<211> LENGTH: 60
<212> TYPE: DNA
<213> ORGANISM: Artificial Sequence
<220> FEATURE:
<223> OTHER INFORMATION: Synthetic

<400> SEQUENCE: 45
cgacccggtc gtcggttcag gacatgtcaa ctcctgcgtg cggccttgac tctcgtacct    60

<210> SEQ ID NO 46
<211> LENGTH: 60
<212> TYPE: DNA
<213> ORGANISM: Artificial Sequence
<220> FEATURE:
<223> OTHER INFORMATION: Synthetic

<400> SEQUENCE: 46
cgacccggtc gtcgattcag gacatgtcaa ctcctgcgtg cggccttgac tctcgtacct    60

<210> SEQ ID NO 47

```
<211> LENGTH: 60
<212> TYPE: DNA
<213> ORGANISM: Artificial Sequence
<220> FEATURE:
<223> OTHER INFORMATION: Synthetic

<400> SEQUENCE: 47
cgacccggtc gtcggttcag gacatgtcaa ctcctgcgtg cggccttgac tctcgtacct    60

<210> SEQ ID NO 48
<211> LENGTH: 60
<212> TYPE: DNA
<213> ORGANISM: Artificial Sequence
<220> FEATURE:
<223> OTHER INFORMATION: Synthetic

<400> SEQUENCE: 48
cgacccggtc gtcggttcag gacatgtcaa ctcctgcgtg cggccttgac tctcgtacct    60

<210> SEQ ID NO 49
<211> LENGTH: 60
<212> TYPE: DNA
<213> ORGANISM: Artificial Sequence
<220> FEATURE:
<223> OTHER INFORMATION: Synthetic

<400> SEQUENCE: 49
cgacccggtc gtcggttcag gacatgtcaa ctcctgcgtg cggccttgac tctcgtacct    60

<210> SEQ ID NO 50
<211> LENGTH: 60
<212> TYPE: DNA
<213> ORGANISM: Artificial Sequence
<220> FEATURE:
<223> OTHER INFORMATION: Synthetic

<400> SEQUENCE: 50
cgacccggtc gtcggttcag gacatgtcaa ctcctgcgtg cggccttgac tctcgtacct    60

<210> SEQ ID NO 51
<211> LENGTH: 60
<212> TYPE: DNA
<213> ORGANISM: Artificial Sequence
<220> FEATURE:
<223> OTHER INFORMATION: Synthetic

<400> SEQUENCE: 51
cgacccggtc gtcggttcag gacatgtcaa ctcctgcgtg cggccttgac tctcgtacct    60

<210> SEQ ID NO 52
<211> LENGTH: 4
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: 6-amino-5-nitro-3-(1'-beta-D-2'-
      deoxyribofuranosyl)-2(1H)-pyridone

<400> SEQUENCE: 52 cnnt                                                                  4

<210> SEQ ID NO 53
<211> LENGTH: 4
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: 2-amino-8-(1'-beta-D-2'-deoxyribofuranosyl)-
      imidazo[1,2-a]-1,3,5-triazin-4(8H)one

<400> SEQUENCE: 53 anng                                                                       4

<210> SEQ ID NO 54
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (7)..(7)
<223> OTHER INFORMATION: 6-amino-5-nitro-3-(1'-beta-D-2'-
      deoxyribofuranosyl)-2(1H)-pyridone

<400> SEQUENCE: 54 gnggccnc                                                                   8

<210> SEQ ID NO 55
<211> LENGTH: 4
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (3)..(3)
<223> OTHER INFORMATION: 6-amino-5-nitro-3-(1'-beta-D-2'-
      deoxyribofuranosyl)-2(1H)-pyridone

<400> SEQUENCE: 55 tnng                                                                       4

<210> SEQ ID NO 56
<211> LENGTH: 4
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (3)..(3)
<223> OTHER INFORMATION: 6-amino-5-nitro-3-(1'-beta-D-2'-
      deoxyribofuranosyl)-2(1H)-pyridone

<400> SEQUENCE: 56 cnna                                                                       4
```

-continued

```
<210> SEQ ID NO 57
<211> LENGTH: 4
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (3)..(3)
<223> OTHER INFORMATION: 2-amino-8-(1'-beta-D-2'-deoxyribofuranosyl)-
      imidazo[1,2-a]-1,3,5-triazin-4(8H)one

<400> SEQUENCE: 57 tnng                                                                      4

<210> SEQ ID NO 58
<211> LENGTH: 4
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (3)..(2)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (3)..(3)
<223> OTHER INFORMATION: 2-amino-8-(1'-beta-D-2'-deoxyribofuranosyl)-
      imidazo[1,2-a]-1,3,5-triazin-4(8H)one

<400> SEQUENCE: 58 cnna                                                                      4

<210> SEQ ID NO 59
<211> LENGTH: 5
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2-amino-8-(1'-beta-D-2'-deoxyribofuranosyl)-
      imidazo[1,2-a]-1,3,5-triazin-4(8H)one
<220> FEATURE:
<221> NAME/KEY: misc_feature
<222> LOCATION: (4)..(4)
<223> OTHER INFORMATION: n =
      2-amino-8-(1'-beta-D-2'-deoxyribofuranosyl)-imidazo[1,2-a]-1,3,5-
      triazin-4(8H)one

<400> SEQUENCE: 59 cntnc                                                                     5

<210> SEQ ID NO 60
<211> LENGTH: 5
<212> TYPE: DNA
<213> ORGANISM: Artificial Sequence
<220> FEATURE:
<223> OTHER INFORMATION: Synthetic
```

-continued

```
<220> FEATURE:
<221> NAME/KEY: misc_feature
<222> LOCATION: (2)..(2)
<223> OTHER INFORMATION: 6-amino-5-nitro-3-(1'-beta-D-2'-
      deoxyribofuranosyl)-2(1H)-pyridone
<220> FEATURE:
<221> NAME/KEY: misc_feature
<222> LOCATION: (4)..(4)
<223> OTHER INFORMATION: 6-amino-5-nitro-3-(1'-beta-D-2'-
      deoxyribofuranosyl)-2(1H)-pyridone

<400> SEQUENCE: 60 gnang                                                                    5

<210> SEQ ID NO 61
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: n = b, nonstandard nucleotide of the invention
<220> FEATURE:
<221> NAME/KEY: misc_feature
<222> LOCATION: (26)..(26)
<223> OTHER INFORMATION: n = s, nonstandard nucleotide of the invention

<400> SEQUENCE: 61
catgtctgat cctgcactgc tgngcncttg actctcgtac ctg                          43

<210> SEQ ID NO 62
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: n = s, nonstandard nucleotide of the invention
<220> FEATURE:
<221> NAME/KEY: misc_feature
<222> LOCATION: (22)..(22)
<223> OTHER INFORMATION: n = b, nonstandard nucleotide of the invention

<400> SEQUENCE: 62
agactaggac gtgacgacnc gngaactgag agcatggact cg                           42

<210> SEQ ID NO 63
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: n = s, nonstandard nucleotide of the invention
<220> FEATURE:
<221> NAME/KEY: misc_feature
<222> LOCATION: (27)..(27)
<223> OTHER INFORMATION: n = b, nonstandard nucleotide of the invention

<400> SEQUENCE: 63
catgtctgat cctgcactgc tnttaanttg actctcgtac ctg                          43

<210> SEQ ID NO 64
<211> LENGTH: 42
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: n = b, nonstandard nucleotide of the invention
<220> FEATURE:
<221> NAME/KEY: misc_feature
<222> LOCATION: (23)..(23)
<223> OTHER INFORMATION: n = s, nonstandard nucleotide of the invention

<400> SEQUENCE: 64
agactaggac gtgacganaa ttnaactgag agcatggact cg                             42

<210> SEQ ID NO 65
<211> LENGTH: 7
<212> TYPE: DNA
<213> ORGANISM: Artificial Sequence
<220> FEATURE:
<223> OTHER INFORMATION: Synthetic

<400> SEQUENCE: 65 gggccct                                                                    7

<210> SEQ ID NO 66
<211> LENGTH: 7
<212> TYPE: DNA
<213> ORGANISM: Artificial Sequence
<220> FEATURE:
<223> OTHER INFORMATION: Synthetic

<400> SEQUENCE: 66 agggccc                                                                    7

<210> SEQ ID NO 67
<211> LENGTH: 7
<212> TYPE: DNA
<213> ORGANISM: Artificial Sequence
<220> FEATURE:
<223> OTHER INFORMATION: Synthetic

<400> SEQUENCE: 67 ggggccc                                                                    7

<210> SEQ ID NO 68
<211> LENGTH: 4
<212> TYPE: DNA
<213> ORGANISM: Artificial Sequence
<220> FEATURE:
<223> OTHER INFORMATION: Synthetic

<400> SEQUENCE: 68 tgcg                                                                       4

<210> SEQ ID NO 69
<211> LENGTH: 4
<212> TYPE: DNA
<213> ORGANISM: Artificial Sequence
<220> FEATURE:
<223> OTHER INFORMATION: Synthetic

<400> SEQUENCE: 69 cgca                                                                       4

<210> SEQ ID NO 70
<211> LENGTH: 4
```

```
<212> TYPE: DNA
<213> ORGANISM: Artificial Sequence
<220> FEATURE:
<223> OTHER INFORMATION: Synthetic

<400> SEQUENCE: 70 tcgg                                                                        4

<210> SEQ ID NO 71
<211> LENGTH: 4
<212> TYPE: DNA
<213> ORGANISM: Artificial Sequence
<220> FEATURE:
<223> OTHER INFORMATION: Synthetic

<400> SEQUENCE: 71 ccga                                                                        4

<210> SEQ ID NO 72
<211> LENGTH: 5
<212> TYPE: DNA
<213> ORGANISM: Artificial Sequence
<220> FEATURE:
<223> OTHER INFORMATION: Synthetic

<400> SEQUENCE: 72 cgtgc                                                                       5

<210> SEQ ID NO 73
<211> LENGTH: 5
<212> TYPE: DNA
<213> ORGANISM: Artificial Sequence
<220> FEATURE:
<223> OTHER INFORMATION: Synthetic

<400> SEQUENCE: 73 gcacg                                                                       5

<210> SEQ ID NO 74
<211> LENGTH: 58
<212> TYPE: DNA
<213> ORGANISM: Artificial Sequence
<220> FEATURE:
<223> OTHER INFORMATION: Synthetic

<400> SEQUENCE: 74
gcactgctgg gcccttgact ctcgtacctg agcggaagag cgcgcaacgc aattaatg            58

<210> SEQ ID NO 75
<211> LENGTH: 57
<212> TYPE: DNA
<213> ORGANISM: Artificial Sequence
<220> FEATURE:
<223> OTHER INFORMATION: Synthetic

<400> SEQUENCE: 75
gcactgctgg gctttgactc tcgtacctga gcggaagagc gcgcaacgca attaatg             57

<210> SEQ ID NO 76
<211> LENGTH: 58
<212> TYPE: DNA
<213> ORGANISM: Artificial Sequence
<220> FEATURE:
<223> OTHER INFORMATION: Synthetic

<400> SEQUENCE: 76
```

```
gcactgctgg gcttttgact ctcgtacctg agcggaagag cgcgcaacgc aattaatg        58
```

<210> SEQ ID NO 77
<211> LENGTH: 58
<212> TYPE: DNA
<213> ORGANISM: Artificial Sequence
<220> FEATURE:
<223> OTHER INFORMATION: Synthetic

<400> SEQUENCE: 77

```
gcactgctga ggcctcgact ctcgtacctg agcggaagag cgcgcaacgc aattaatg        58
```

<210> SEQ ID NO 78
<211> LENGTH: 58
<212> TYPE: DNA
<213> ORGANISM: Artificial Sequence
<220> FEATURE:
<223> OTHER INFORMATION: Synthetic

<400> SEQUENCE: 78

```
gcactgctgg gcttttgact ctcgtacctg agcggaagag cgcgcaacgc aattaatg        58
```

<210> SEQ ID NO 79
<211> LENGTH: 57
<212> TYPE: DNA
<213> ORGANISM: Artificial Sequence
<220> FEATURE:
<223> OTHER INFORMATION: Synthetic

<400> SEQUENCE: 79

```
gcactgctgg gctttgactc tcgtacctga gcggaagagc gcgcaacgca attaatg         57
```

<210> SEQ ID NO 80
<211> LENGTH: 57
<212> TYPE: DNA
<213> ORGANISM: Artificial Sequence
<220> FEATURE:
<223> OTHER INFORMATION: Synthetic

<400> SEQUENCE: 80

```
gcactgctgg gctttgactc tcgtacctga gcggaagagc gcgcaacgca attaatg         57
```

<210> SEQ ID NO 81
<211> LENGTH: 57
<212> TYPE: DNA
<213> ORGANISM: Artificial Sequence
<220> FEATURE:
<223> OTHER INFORMATION: Synthetic

<400> SEQUENCE: 81

```
gcactgctgg gctttgactc tcgtacctga gcggaagagc gcgcaacgca attaatg         57
```

<210> SEQ ID NO 82
<211> LENGTH: 57
<212> TYPE: DNA
<213> ORGANISM: Artificial Sequence
<220> FEATURE:
<223> OTHER INFORMATION: Synthetic

<400> SEQUENCE: 82

```
gcactgctgg gctttgatga ctctcgtaga gcggaagagc gcgcaacgca attaatg         57
```

<210> SEQ ID NO 83
<211> LENGTH: 58
<212> TYPE: DNA
<213> ORGANISM: Artificial Sequence
<220> FEATURE:
<223> OTHER INFORMATION: Synthetic

<400> SEQUENCE: 83
gcactgctgg gcttttgact ctcgtacctg agcggaagag cgcgcaacgc aattaatg    58

<210> SEQ ID NO 84
<211> LENGTH: 57
<212> TYPE: DNA
<213> ORGANISM: Artificial Sequence
<220> FEATURE:
<223> OTHER INFORMATION: Synthetic

<400> SEQUENCE: 84
gcactgctgg gctttgactc tcgtacctga gcggaagagc gcgcaacgca attaatg     57

<210> SEQ ID NO 85
<211> LENGTH: 57
<212> TYPE: DNA
<213> ORGANISM: Artificial Sequence
<220> FEATURE:
<223> OTHER INFORMATION: Synthetic

<400> SEQUENCE: 85
gcactgctgg gctttgactc tcgtacctga gcggaagagc gcgcaacgca attaatg     57

<210> SEQ ID NO 86
<211> LENGTH: 58
<212> TYPE: DNA
<213> ORGANISM: Artificial Sequence
<220> FEATURE:
<223> OTHER INFORMATION: Synthetic

<400> SEQUENCE: 86
gcactgctga ggcctcgact ctcgtacctg agcggaagag cgcgcaacgc aattaatg    58

<210> SEQ ID NO 87
<211> LENGTH: 67
<212> TYPE: DNA
<213> ORGANISM: Artificial Sequence
<220> FEATURE:
<223> OTHER INFORMATION: Synthetic

<400> SEQUENCE: 87
cggttcagga catgtctgat cctgcactgc tggggcccct tgactctcgt acctgagcgg    60
aagagcg                                                              67

<210> SEQ ID NO 88
<211> LENGTH: 67
<212> TYPE: DNA
<213> ORGANISM: Artificial Sequence
<220> FEATURE:
<223> OTHER INFORMATION: Synthetic

<400> SEQUENCE: 88
cggttcagga catgtctgat cctgcactgc tgaggcctct tgactctcgt acctgagcgg    60
aagagcg                                                              67

<210> SEQ ID NO 89
<211> LENGTH: 65
<212> TYPE: DNA
<213> ORGANISM: Artificial Sequence
<220> FEATURE:
<223> OTHER INFORMATION: Synthetic

```
<400> SEQUENCE: 89
cggttcagga catgtcgatc ctgcactgct gaggcctctt gactctcgac ctgagcggaa    60
gagcg                                                                65

<210> SEQ ID NO 90
<211> LENGTH: 67
<212> TYPE: DNA
<213> ORGANISM: Artificial Sequence
<220> FEATURE:
<223> OTHER INFORMATION: Synthetic

<400> SEQUENCE: 90
cggttcagga catgtctgat cctgcactgc tgaggcctct tgactctcgt acctgagcgg    60
aagagcg                                                              67

<210> SEQ ID NO 91
<211> LENGTH: 66
<212> TYPE: DNA
<213> ORGANISM: Artificial Sequence
<220> FEATURE:
<223> OTHER INFORMATION: Synthetic

<400> SEQUENCE: 91
cggttcagga catgctgatc ctgcactgct gaggcctctt gactctcgta cctgagcgga    60
agagcg                                                               66

<210> SEQ ID NO 92
<211> LENGTH: 67
<212> TYPE: DNA
<213> ORGANISM: Artificial Sequence
<220> FEATURE:
<223> OTHER INFORMATION: Synthetic

<400> SEQUENCE: 92
cggttcagga catgtctgat cctgcactgc tgaggcctct tgactctcgt acctgagcgg    60
aagagcg                                                              67

<210> SEQ ID NO 93
<211> LENGTH: 67
<212> TYPE: DNA
<213> ORGANISM: Artificial Sequence
<220> FEATURE:
<223> OTHER INFORMATION: Synthetic

<400> SEQUENCE: 93
aggttcagga catgtctgat cctgcactgc tgaggcctct tgactctcgt acctgagcgg    60
aagagcg                                                              67

<210> SEQ ID NO 94
<211> LENGTH: 65
<212> TYPE: DNA
<213> ORGANISM: Artificial Sequence
<220> FEATURE:
<223> OTHER INFORMATION: Synthetic

<400> SEQUENCE: 94
cttgcaaagg ggaggatgtc tgcactgctg aggcctcttg actctcgtac ctgagcggaa    60
gagcg                                                                65

<210> SEQ ID NO 95
<211> LENGTH: 67
```

```
<212> TYPE: DNA
<213> ORGANISM: Artificial Sequence
<220> FEATURE:
<223> OTHER INFORMATION: Synthetic

<400> SEQUENCE: 95
cggttcagga catgtctgat cctgcactgc tgaggcctct tgactctcgt acctgagcgg    60
aagagcg                                                              67

<210> SEQ ID NO 96
<211> LENGTH: 67
<212> TYPE: DNA
<213> ORGANISM: Artificial Sequence
<220> FEATURE:
<223> OTHER INFORMATION: Synthetic

<400> SEQUENCE: 96
cggttcagga catgtctgat cctgcactgc tgaggcctct tgactctcgt acctgagcgg    60
aagagcg                                                              67

<210> SEQ ID NO 97
<211> LENGTH: 67
<212> TYPE: DNA
<213> ORGANISM: Artificial Sequence
<220> FEATURE:
<223> OTHER INFORMATION: Synthetic

<400> SEQUENCE: 97
cggttcagga catgtctgat cctgcactgc tgaggcctct tgactctcgt acctgagcgg    60
aagagcg                                                              67

<210> SEQ ID NO 98
<211> LENGTH: 67
<212> TYPE: DNA
<213> ORGANISM: Artificial Sequence
<220> FEATURE:
<223> OTHER INFORMATION: Synthetic

<400> SEQUENCE: 98
cggttcagga catgtctgat cctgcactgc tgaggcctct tgactctcgt acctgagcgg    60
aagagcg                                                              67

<210> SEQ ID NO 99
<211> LENGTH: 67
<212> TYPE: DNA
<213> ORGANISM: Artificial Sequence
<220> FEATURE:
<223> OTHER INFORMATION: Synthetic

<400> SEQUENCE: 99
cggttcagga catgtctgat cctgcactgc tgaggcctct tgactctcgt acctgagcgg    60
aagagcg                                                              67

<210> SEQ ID NO 100
<211> LENGTH: 66
<212> TYPE: DNA
<213> ORGANISM: Artificial Sequence
<220> FEATURE:
<223> OTHER INFORMATION: Synthetic

<400> SEQUENCE: 100
cggttcagga catgtctgat cctcactgct gaggcctctt gactctcgta cctgagcgga    60
``` agagcg 66

<210> SEQ ID NO 101
<211> LENGTH: 67
<212> TYPE: DNA
<213> ORGANISM: Artificial Sequence
<220> FEATURE:
<223> OTHER INFORMATION: Synthetic

<400> SEQUENCE: 101
cggttcagga catgtctgat cctgcactgc tgaggcctct tgactctcgt acctgagcgg    60
aagagcg    67

<210> SEQ ID NO 102
<211> LENGTH: 66
<212> TYPE: DNA
<213> ORGANISM: Artificial Sequence
<220> FEATURE:
<223> OTHER INFORMATION: Synthetic

<400> SEQUENCE: 102
cggttcagga catgttgatc ctgcactgct gaggcctctt gactctcgta cctgagcgga    60
agagcg    66

<210> SEQ ID NO 103
<211> LENGTH: 67
<212> TYPE: DNA
<213> ORGANISM: Artificial Sequence
<220> FEATURE:
<223> OTHER INFORMATION: Synthetic

<400> SEQUENCE: 103
cggttcagga catgtctgat cctgcactgc tgaggcctct tgactctcgt acctgagcgg    60
aagagcg    67

<210> SEQ ID NO 104
<211> LENGTH: 59
<212> TYPE: DNA
<213> ORGANISM: Artificial Sequence
<220> FEATURE:
<223> OTHER INFORMATION: Synthetic

<400> SEQUENCE: 104
tcgacccggt cgtcggttca ggacatgtca actcctgcgt gcggccttga ctctcgtac    59

<210> SEQ ID NO 105
<211> LENGTH: 57
<212> TYPE: DNA
<213> ORGANISM: Artificial Sequence
<220> FEATURE:
<223> OTHER INFORMATION: Synthetic

<400> SEQUENCE: 105
tcgacccggt cgtcggttca ggacatgtca actcctatgc ggccttgact ctcgtac    57

<210> SEQ ID NO 106
<211> LENGTH: 59
<212> TYPE: DNA
<213> ORGANISM: Artificial Sequence
<220> FEATURE:
<223> OTHER INFORMATION: Synthetic

<400> SEQUENCE: 106
tcgacccggt cgtcggttca ggacatgtca actcctgcgt gtggccttga ctctcgtac    59

<210> SEQ ID NO 107
<211> LENGTH: 59
<212> TYPE: DNA
<213> ORGANISM: Artificial Sequence
<220> FEATURE:
<223> OTHER INFORMATION: Synthetic

<400> SEQUENCE: 107
tcgacccggt cgtcggttca ggacatgtca actcctgcgt atggccttga ctctcgtac    59

<210> SEQ ID NO 108
<211> LENGTH: 59
<212> TYPE: DNA
<213> ORGANISM: Artificial Sequence
<220> FEATURE:
<223> OTHER INFORMATION: Synthetic

<400> SEQUENCE: 108
tcgacccggt cgtcggttca ggacatgtca tctcctgcgt atggccttga ctctcgtac    59

<210> SEQ ID NO 109
<211> LENGTH: 58
<212> TYPE: DNA
<213> ORGANISM: Artificial Sequence
<220> FEATURE:
<223> OTHER INFORMATION: Synthetic

<400> SEQUENCE: 109
tcgacccggt cgtcgttcag gacatgtcaa ctcctgcgta tggccttaac tctcgtac     58

<210> SEQ ID NO 110
<211> LENGTH: 59
<212> TYPE: DNA
<213> ORGANISM: Artificial Sequence
<220> FEATURE:
<223> OTHER INFORMATION: Synthetic

<400> SEQUENCE: 110
tcgacccggt cgtcggttca ggacatgtca actcctgcat atggccttga ctctcgtac    59

<210> SEQ ID NO 111
<211> LENGTH: 66
<212> TYPE: DNA
<213> ORGANISM: Artificial Sequence
<220> FEATURE:
<223> OTHER INFORMATION: Synthetic

<400> SEQUENCE: 111
catgtcaact cctgcgtcgg gccttgactc tcgtacctga gcggaagagc gcgaacgca    60 attaat                                                              66

<210> SEQ ID NO 112
<211> LENGTH: 66
<212> TYPE: DNA
<213> ORGANISM: Artificial Sequence
<220> FEATURE:
<223> OTHER INFORMATION: Synthetic

<400> SEQUENCE: 112
catgtcaact cctgcgtcag gccttgactc tcgtacctga gcggaagagc gcgaacgca    60 attaat                                                              66

<210> SEQ ID NO 113

```
<211> LENGTH: 66
<212> TYPE: DNA
<213> ORGANISM: Artificial Sequence
<220> FEATURE:
<223> OTHER INFORMATION: Synthetic

<400> SEQUENCE: 113
catgtcaact cctgcgttag gccttgactc tcgtacctga gcggaagagc gcgcaacgca    60
attaat                                                              66

<210> SEQ ID NO 114
<211> LENGTH: 65
<212> TYPE: DNA
<213> ORGANISM: Artificial Sequence
<220> FEATURE:
<223> OTHER INFORMATION: Synthetic

<400> SEQUENCE: 114
catgtcaact cctgcgttgg ccttgactct cgtacctgag cggaagagcg cgcaacgcaa    60
ttaat                                                               65

<210> SEQ ID NO 115
<211> LENGTH: 70
<212> TYPE: DNA
<213> ORGANISM: Artificial Sequence
<220> FEATURE:
<223> OTHER INFORMATION: Synthetic

<400> SEQUENCE: 115
ggttcaggac atgtcaactc ctgcgtgcgg ccttgactct cgtacctgag cggaagagcg    60
cgcaacgcaa                                                          70

<210> SEQ ID NO 116
<211> LENGTH: 70
<212> TYPE: DNA
<213> ORGANISM: Artificial Sequence
<220> FEATURE:
<223> OTHER INFORMATION: Synthetic

<400> SEQUENCE: 116
ggttcaggac atgtcaactc ctgcatacgg ccttgactct cgtacctgag cggaagagcg    60
cgcaacgcaa                                                          70

<210> SEQ ID NO 117
<211> LENGTH: 69
<212> TYPE: DNA
<213> ORGANISM: Artificial Sequence
<220> FEATURE:
<223> OTHER INFORMATION: Synthetic

<400> SEQUENCE: 117
ggttcaggac atgtcaatcc tgcatacggc cttgactctc gtacctgagc ggaagagcgc    60
gcaacgcaa                                                           69

<210> SEQ ID NO 118
<211> LENGTH: 69
<212> TYPE: DNA
<213> ORGANISM: Artificial Sequence
<220> FEATURE:
<223> OTHER INFORMATION: Synthetic

<400> SEQUENCE: 118
ggttcaggac atgtcaactc ctgcatacgg ccttgactct cgtacctgag cggaagagcg    60
```

<210> SEQ ID NO 119
<211> LENGTH: 862
<212> TYPE: DNA
<213> ORGANISM: Artificial Sequence
<220> FEATURE:
<223> OTHER INFORMATION: Synthetic

<400> SEQUENCE: 119

```
accatgagcc atattcaacg ggaaacgtcg aggccgcgat taaattccaa catggatgct      60
gatttatatg ggtataaatg ggctcgcgat aatgtcgggc aatcaggtgc gacaatctat     120
cgcttgtatg ggaagcccga tgcgccagag ttgtttctga aacatggcaa aggtagcgtt     180
gccaatgatg ttacagatga gatggtcaga ctaaactggc tgacggaatt tatgcctctt     240
ccgaccatca agcattttat ccgtactcct gatgatgcat ggttactcac cactgcgatc     300
cccggaaaaa cagcattcca ggtattagaa gaatatcctg attcaggtga aaatattgtt     360
gatgcgctgg cagtgttcct gcgccggttg cattcgattc ctgtttgtaa ttgtccttt      420
aacagcgatc gcgtatttcg tctcgctcag gcgcaatcac gaatgaataa cggtttggtt     480
gatgcgagtg attttgatga cgagcgtaat ggctggcctg ttgaacaagt ctggaaagaa     540
atgcataaac ttttgccatt ctcaccggat tcagtcgtca ctcatggtga tttctcactt     600
gataaccta ttttttgacga ggggaaatta ataggttgta ttgatgttgg acgagtcgga    660
atcgcagacc gataccagga tcttgccatc ctatggaact gcctcggtga gttttctcct     720
tcattacaga aacggctttt tcaaaaatat ggtattgata atcctgatat gaataaattg     780
cagtttcatt tgatgctcga tgagttttc taacaatgta agcacgacta gcagctgaca     840
ggacggacag atcgaccact ag                                              862
```

<210> SEQ ID NO 120
<211> LENGTH: 863
<212> TYPE: DNA
<213> ORGANISM: Artificial Sequence
<220> FEATURE:
<223> OTHER INFORMATION: Synthetic

<400> SEQUENCE: 120

```
caccatgagc catattcaac gggaaacgtc gaggccgcga ttaaattcca acatggasgc      60
sgasttatat gggtataaat gggctcgcga taasgtcggg cabtcbggtg cgacaatcta     120
tcgcttgtat gggaagcccg asgcgccbga gttgtttctg aaacatggca aaggtagcgt     180
sgccaasgas gtsacagatg agatggtcag actaaactgg ctgacggabt ttatgccsct     240
sccgaccatc aagcattta tccgsacscc sgasgatgca tggttactca ccactgcgat     300
ccccggbaaa acbgcbttcc aggtattaga agaatatcct gattcaggsg abaasattgt     360
sgatgcgctg gcagtgttcc tgcgccggtt gcastcgatt cctgtstgta attgtccttt     420
taacagcgat cgcgtatttc gsctcgcsca ggcgcaatca cgaatgaata acggsttggt     480
sgasgcgagt gattttgatg acgagcgtaa tggctggccs gtsgabcabg tctggaaaga     540
aatgcasaab ctsttgccbt tctcaccgga ttcagtcgtc actcatggtg asttctcbct     600
sgasaacctt attttgacg aggggaaatt aataggttgt attgasgttg gacgbgtcgg     660
aatcgcagac cgbtaccagg asctsgccat cctatggaac tgcctcggtg agttttctcc     720
stcbttacag aabcggcttt tcaaaaata tggtattgat aatccsgasa tgaasaabtt     780
```

```
gcagtttcat tgatgctcg atgagttttt ctaacaggat ccgcbcgbcs agcagctgac      840
aggacggacb gascgbccbc tag                                             863
```

<210> SEQ ID NO 121
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (58)..(58)
<223> OTHER INFORMATION: s = nonstandard nucleotide of the invention
<220> FEATURE:
<221> NAME/KEY: misc_feature
<222> LOCATION: (61)..(61)
<223> OTHER INFORMATION: s = nonstandard nucleotide of the invention
<220> FEATURE:
<221> NAME/KEY: misc_feature
<222> LOCATION: (64)..(64)
<223> OTHER INFORMATION: s = nonstandard nucleotide of the invention

<400> SEQUENCE: 121

```
caccatgagc catattcaac gggaaacgtc gaggccgcga ttaaattcca acatggasgc      60 sgastt                                                                66
```

<210> SEQ ID NO 122
<211> LENGTH: 58
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: s = nonstandard nucleotide of the invention
<220> FEATURE:
<221> NAME/KEY: misc_feature
<222> LOCATION: (10)..(10)
<223> OTHER INFORMATION: b = nonstandard nucleotide of the invention
<220> FEATURE:
<221> NAME/KEY: misc_feature
<222> LOCATION: (13)..(13)
<223> OTHER INFORMATION: b = nonstandard nucleotide of the invention
<220> FEATURE:
<221> NAME/KEY: misc_feature
<222> LOCATION: (49)..(49)
<223> OTHER INFORMATION: s = nonstandard nucleotide of the invention
<220> FEATURE:
<221> NAME/KEY: misc_feature
<222> LOCATION: (55)..(55)
<223> OTHER INFORMATION: b = nonstandard nucleotide of the invention

<400> SEQUENCE: 122

```
sgtcgggcab tcbggtgcga caatctatcg cttgtatggg aagcccgasg cgccbgag        58
```

<210> SEQ ID NO 123
<211> LENGTH: 62
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: s = nonstandard nucleotide of the invention
<220> FEATURE:
<221> NAME/KEY: misc_feature
<222> LOCATION: (7)..(7)
<223> OTHER INFORMATION: s = nonstandard nucleotide of the invention
<220> FEATURE:
<221> NAME/KEY: misc_feature

```
<222> LOCATION: (10)..(10)
<223> OTHER INFORMATION: s = nonstandard nucleotide of the invention
<220> FEATURE:
<221> NAME/KEY: misc_feature
<222> LOCATION: (13)..(13)
<223> OTHER INFORMATION: s = nonstandard nucleotide of the invention
<220> FEATURE:
<221> NAME/KEY: misc_feature
<222> LOCATION: (49)..(49)
<223> OTHER INFORMATION: b = nonstandard nucleotide of the invention
<220> FEATURE:
<221> NAME/KEY: misc_feature
<222> LOCATION: (58)..(58)
<223> OTHER INFORMATION: s = nonstandard nucleotide of the invention
<220> FEATURE:
<221> NAME/KEY: misc_feature
<222> LOCATION: (61)..(61)
<223> OTHER INFORMATION: s = nonstandard nucleotide of the invention

<400> SEQUENCE: 123
sgccaasgas gtsacagatg agatggtcag actaaactgg ctgacggabt ttatgccsct    60 sc                                                                  62

<210> SEQ ID NO 124
<211> LENGTH: 54
<212> TYPE: DNA
<213> ORGANISM: Artificial Sequence
<220> FEATURE:
<223> OTHER INFORMATION: Synthesis
<220> FEATURE:
<221> NAME/KEY: misc_feature
<222> LOCATION: (1)..(1)
<223> OTHER INFORMATION: s = nonstandard nucleotide of the invention
<220> FEATURE:
<221> NAME/KEY: misc_feature
<222> LOCATION: (4)..(4)
<223> OTHER INFORMATION: s = nonstandard nucleotide of the invention
<220> FEATURE:
<221> NAME/KEY: misc_feature
<222> LOCATION: (7)..(7)
<223> OTHER INFORMATION: s = nonstandard nucleotide of the invention
<220> FEATURE:
<221> NAME/KEY: misc_feature
<222> LOCATION: (10)..(10)
<223> OTHER INFORMATION: s = nonstandard nucleotide of the invention
<220> FEATURE:
<221> NAME/KEY: misc_feature
<222> LOCATION: (43)..(43)
<223> OTHER INFORMATION: b = nonstandard nucleotide of the invention
<220> FEATURE:
<221> NAME/KEY: misc_feature
<222> LOCATION: (49)..(49)
<223> OTHER INFORMATION: b = nonstandard nucleotide of the invention
<220> FEATURE:
<221> NAME/KEY: misc_feature
<222> LOCATION: (52)..(52)
<223> OTHER INFORMATION: b = nonstandard nucleotide of the invention

<400> SEQUENCE: 124
sacsccsgas gatgcatggt tactcaccac tgcgatcccc ggbaaaacbg cbtt          54

<210> SEQ ID NO 125
<211> LENGTH: 59
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: s = nonstandard nucleotide of the invention
<220> FEATURE:
<221> NAME/KEY: misc_feature
<222> LOCATION: (4)..(4)
```

<223> OTHER INFORMATION: b = nonstandard nucleotide of the invention
<220> FEATURE:
<221> NAME/KEY: misc_feature
<222> LOCATION: (7)..(7)
<223> OTHER INFORMATION: s = nonstandard nucleotide of the invention
<220> FEATURE:
<221> NAME/KEY: misc_feature
<222> LOCATION: (13)..(13)
<223> OTHER INFORMATION: s = nonstandard nucleotide of the invention
<220> FEATURE:
<221> NAME/KEY: misc_feature
<222> LOCATION: (46)..(46)
<223> OTHER INFORMATION: s = nonstandard nucleotide of the invention
<220> FEATURE:
<221> NAME/KEY: misc_feature
<222> LOCATION: (58)..(58)
<223> OTHER INFORMATION: s = nonstandard nucleotide of the invention

<400> SEQUENCE: 125
sgabaasatt gtsgatgcgc tggcagtgtt cctgcgccgg ttgcastcga ttcctgtst            59

<210> SEQ ID NO 126
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: s = nonstandard nucleotide of the invention
<220> FEATURE:
<221> NAME/KEY: misc_feature
<222> LOCATION: (10)..(10)
<223> OTHER INFORMATION: s = nonstandard nucleotide of the invention
<220> FEATURE:
<221> NAME/KEY: misc_feature
<222> LOCATION: (37)..(37)
<223> OTHER INFORMATION: s = nonstandard nucleotide of the invention
<220> FEATURE:
<221> NAME/KEY: misc_feature
<222> LOCATION: (43)..(43)
<223> OTHER INFORMATION: s = nonstandard nucleotide of the invention
<220> FEATURE:
<221> NAME/KEY: misc_feature
<222> LOCATION: (46)..(46)
<223> OTHER INFORMATION: s = nonstandard nucleotide of the invention

<400> SEQUENCE: 126
tcgsctcgcs caggcgcaat cacgaatgaa taacggsttg gtsgasg                        47

<210> SEQ ID NO 127
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: s = nonstandard nucleotide of the invention
<220> FEATURE:
<221> NAME/KEY: misc_feature
<222> LOCATION: (4)..(4)
<223> OTHER INFORMATION: s = nonstandard nucleotide of the invention
<220> FEATURE:
<221> NAME/KEY: misc_feature
<222> LOCATION: (7)..(7)
<223> OTHER INFORMATION: b = nonstandard nucleotide of the invention
<220> FEATURE:
<221> NAME/KEY: misc_feature

```
<222> LOCATION: (10)..(10)
<223> OTHER INFORMATION: b = nonstandard nucleotide of the invention
<220> FEATURE:
<221> NAME/KEY: misc_feature
<222> LOCATION: (28)..(28)
<223> OTHER INFORMATION: s = nonstandard nucleotide of the invention
<220> FEATURE:
<221> NAME/KEY: misc_feature
<222> LOCATION: (31)..(31)
<223> OTHER INFORMATION: b = nonstandard nucleotide of the invention
<220> FEATURE:
<221> NAME/KEY: misc_feature
<222> LOCATION: (34)..(34)
<223> OTHER INFORMATION: s = nonstandard nucleotide of the invention
<220> FEATURE:
<221> NAME/KEY: misc_feature
<222> LOCATION: (40)..(40)
<223> OTHER INFORMATION: b = nonstandard nucleotide of the invention

<400> SEQUENCE: 127
sgtsgabcab gtctggaaag aaatgcasaa bctsttgccb t                          41

<210> SEQ ID NO 128
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: s = nonstandard nucleotide of the invention
<220> FEATURE:
<221> NAME/KEY: misc_feature
<222> LOCATION: (8)..(8)
<223> OTHER INFORMATION: b = nonstandard nucleotide of the invention
<220> FEATURE:
<221> NAME/KEY: misc_feature
<222> LOCATION: (11)..(11)
<223> OTHER INFORMATION: s = nonstandard nucleotide of the invention
<220> FEATURE:
<221> NAME/KEY: misc_feature
<222> LOCATION: (14)..(14)
<223> OTHER INFORMATION: s = nonstandard nucleotide of the invention
<220> FEATURE:
<221> NAME/KEY: misc_feature
<222> LOCATION: (56)..(56)
<223> OTHER INFORMATION: s = nonstandard nucleotide of the invention
<220> FEATURE:
<221> NAME/KEY: misc_feature
<222> LOCATION: (65)..(65)
<223> OTHER INFORMATION: b = nonstandard nucleotide of the invention

<400> SEQUENCE: 128
asttctcbct sgasaacctt atttttgacg aggggaaatt aataggttgt attgasgttg       60 gacgbgt                                                                67

<210> SEQ ID NO 129
<211> LENGTH: 62
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: b = nonstandard nucleotide of the invention
<220> FEATURE:
<221> NAME/KEY: misc_feature
<222> LOCATION: (10)..(10)
<223> OTHER INFORMATION: s = nonstandard nucleotide of the invention
<220> FEATURE:
<221> NAME/KEY: misc_feature
<222> LOCATION: (13)..(13)
```

```
<223> OTHER INFORMATION: s = nonstandard nucleotide of the invention
<220> FEATURE:
<221> NAME/KEY: misc_feature
<222> LOCATION: (49)..(49)
<223> OTHER INFORMATION: s = nonstandard nucleotide of the invention
<220> FEATURE:
<221> NAME/KEY: misc_feature
<222> LOCATION: (52)..(52)
<223> OTHER INFORMATION: b = nonstandard nucleotide of the invention
<220> FEATURE:
<221> NAME/KEY: misc_feature
<222> LOCATION: (61)..(61)
<223> OTHER INFORMATION: b = nonstandard nucleotide of the invention

<400> SEQUENCE: 129
btaccaggas ctsgccatcc tatggaactg cctcggtgag ttttctccst cbttacagaa      60 bc                                                                     62

<210> SEQ ID NO 130
<211> LENGTH: 68
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: s = nonstandard nucleotide of the invention
<220> FEATURE:
<221> NAME/KEY: misc_feature
<222> LOCATION: (5)..(5)
<223> OTHER INFORMATION: s = nonstandard nucleotide of the invention
<220> FEATURE:
<221> NAME/KEY: misc_feature
<222> LOCATION: (11)..(11)
<223> OTHER INFORMATION: s = nonstandard nucleotide of the invention
<220> FEATURE:
<221> NAME/KEY: misc_feature
<222> LOCATION: (14)..(14)
<223> OTHER INFORMATION: b = nonstandard nucleotide of the invention
<220> FEATURE:
<221> NAME/KEY: misc_feature
<222> LOCATION: (61)..(61)
<223> OTHER INFORMATION: b = nonstandard nucleotide of the invention
<220> FEATURE:
<221> NAME/KEY: misc_feature
<222> LOCATION: (64)..(64)
<223> OTHER INFORMATION: b = nonstandard nucleotide of the invention
<220> FEATURE:
<221> NAME/KEY: misc_feature
<222> LOCATION: (66)..(66)
<223> OTHER INFORMATION: s = nonstandard nucleotide of the invention

<400> SEQUENCE: 130
csgasatgaa saabttgcag tttcatttga tgctcgatga gtttttctaa caggatccgc      60 bcgbcsag                                                               68

<210> SEQ ID NO 131
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: s = nonstandard nucleotide of the invention
<220> FEATURE:
<221> NAME/KEY: misc_feature
<222> LOCATION: (4)..(4)
<223> OTHER INFORMATION: s = nonstandard nucleotide of the invention
<220> FEATURE:
<221> NAME/KEY: misc_feature
```

```
<222> LOCATION: (13)..(13)
<223> OTHER INFORMATION: b = nonstandard nucleotide of the invention
<220> FEATURE:
<221> NAME/KEY: misc_feature
<222> LOCATION: (43)..(43)
<223> OTHER INFORMATION: b = nonstandard nucleotide of the invention
<220> FEATURE:
<221> NAME/KEY: misc_feature
<222> LOCATION: (46)..(46)
<223> OTHER INFORMATION: b = nonstandard nucleotide of the invention
<220> FEATURE:
<221> NAME/KEY: misc_feature
<222> LOCATION: (49)..(49)
<223> OTHER INFORMATION: b = nonstandard nucleotide of the invention

<400> SEQUENCE: 131
sgastgcccg acbttatcgc gagcccattt atacccatat aabtcbgcbt cc         52

<210> SEQ ID NO 132
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: b = nonstandard nucleotide of the invention
<220> FEATURE:
<221> NAME/KEY: misc_feature
<222> LOCATION: (4)..(4)
<223> OTHER INFORMATION: b = nonstandard nucleotide of the invention
<220> FEATURE:
<221> NAME/KEY: misc_feature
<222> LOCATION: (7)..(7)
<223> OTHER INFORMATION: b = nonstandard nucleotide of the invention
<220> FEATURE:
<221> NAME/KEY: misc_feature
<222> LOCATION: (13)..(13)
<223> OTHER INFORMATION: b = nonstandard nucleotide of the invention
<220> FEATURE:
<221> NAME/KEY: misc_feature
<222> LOCATION: (46)..(46)
<223> OTHER INFORMATION: s = nonstandard nucleotide of the invention
<220> FEATURE:
<221> NAME/KEY: misc_feature
<222> LOCATION: (52)..(52)
<223> OTHER INFORMATION: b = nonstandard nucleotide of the invention

<400> SEQUENCE: 132
bacbtcbttg gcbacgctac ctttgccatg tttcagaaac aactcsggcg cbt        53

<210> SEQ ID NO 133
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: b = nonstandard nucleotide of the invention
<220> FEATURE:
<221> NAME/KEY: misc_feature
<222> LOCATION: (6)..(6)
<223> OTHER INFORMATION: b = nonstandard nucleotide of the invention
<220> FEATURE:
<221> NAME/KEY: misc_feature
<222> LOCATION: (9)..(9)
<223> OTHER INFORMATION: b = nonstandard nucleotide of the invention
<220> FEATURE:
<221> NAME/KEY: misc_feature
<222> LOCATION: (12)..(12)
<223> OTHER INFORMATION: b = nonstandard nucleotide of the invention
<220> FEATURE:
```

```
<221> NAME/KEY: misc_feature
<222> LOCATION: (36)..(36)
<223> OTHER INFORMATION: b = nonstandard nucleotide of the invention
<220> FEATURE:
<221> NAME/KEY: misc_feature
<222> LOCATION: (39)..(39)
<223> OTHER INFORMATION: b = nonstandard nucleotide of the invention
<220> FEATURE:
<221> NAME/KEY: misc_feature
<222> LOCATION: (48)..(48)
<223> OTHER INFORMATION: s = nonstandard nucleotide of the invention

<400> SEQUENCE: 133
tcbtcbggbg tbcggataaa atgcttgatg gtcggbagbg gcataaast                49

<210> SEQ ID NO 134
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: b = nonstandard nucleotide of the invention
<220> FEATURE:
<221> NAME/KEY: misc_feature
<222> LOCATION: (8)..(8)
<223> OTHER INFORMATION: b = nonstandard nucleotide of the invention
<220> FEATURE:
<221> NAME/KEY: misc_feature
<222> LOCATION: (11)..(11)
<223> OTHER INFORMATION: s = nonstandard nucleotide of the invention
<220> FEATURE:
<221> NAME/KEY: misc_feature
<222> LOCATION: (14)..(14)
<223> OTHER INFORMATION: b = nonstandard nucleotide of the invention
<220> FEATURE:
<221> NAME/KEY: misc_feature
<222> LOCATION: (47)..(47)
<223> OTHER INFORMATION: s = nonstandard nucleotide of the invention
<220> FEATURE:
<221> NAME/KEY: misc_feature
<222> LOCATION: (50)..(50)
<223> OTHER INFORMATION: s = nonstandard nucleotide of the invention
<220> FEATURE:
<221> NAME/KEY: misc_feature
<222> LOCATION: (56)..(56)
<223> OTHER INFORMATION: s = nonstandard nucleotide of the invention

<400> SEQUENCE: 134
cbacaatbtt stcbcctgaa tcaggatatt cttctaatac ctggaasgcs gttttsc       57

<210> SEQ ID NO 135
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: b = nonstandard nucleotide of the invention
<220> FEATURE:
<221> NAME/KEY: misc_feature
<222> LOCATION: (8)..(8)
<223> OTHER INFORMATION: b = nonstandard nucleotide of the invention
<220> FEATURE:
<221> NAME/KEY: misc_feature
<222> LOCATION: (44)..(44)
<223> OTHER INFORMATION: b = nonstandard nucleotide of the invention
<220> FEATURE:
<221> NAME/KEY: misc_feature
<222> LOCATION: (56)..(56)
<223> OTHER INFORMATION: b = nonstandard nucleotide of the invention
```

-continued

<400> SEQUENCE: 135
gbgcgagbcg aaatacgcga tcgctgttaa aaggacaatt acabacagga atcgabt    57

<210> SEQ ID NO 136
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: s = nonstandard nucleotide of the invention
<220> FEATURE:
<221> NAME/KEY: misc_feature
<222> LOCATION: (5)..(5)
<223> OTHER INFORMATION: s = nonstandard nucleotide of the invention
<220> FEATURE:
<221> NAME/KEY: misc_feature
<222> LOCATION: (8)..(8)
<223> OTHER INFORMATION: b = nonstandard nucleotide of the invention
<220> FEATURE:
<221> NAME/KEY: misc_feature
<222> LOCATION: (11)..(11)
<223> OTHER INFORMATION: b = nonstandard nucleotide of the invention
<220> FEATURE:
<221> NAME/KEY: misc_feature
<222> LOCATION: (47)..(47)
<223> OTHER INFORMATION: b = nonstandard nucleotide of the invention
<220> FEATURE:
<221> NAME/KEY: misc_feature
<222> LOCATION: (50)..(50)
<223> OTHER INFORMATION: b = nonstandard nucleotide of the invention
<220> FEATURE:
<221> NAME/KEY: misc_feature
<222> LOCATION: (56)..(56)
<223> OTHER INFORMATION: b = nonstandard nucleotide of the invention

<400> SEQUENCE: 136
cstgstcbac bggccagcca ttacgctcgt catcaaaatc actcgcbtcb accaabc    57

<210> SEQ ID NO 137
<211> LENGTH: 59
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: b = nonstandard nucleotide of the invention
<220> FEATURE:
<221> NAME/KEY: misc_feature
<222> LOCATION: (4)..(4)
<223> OTHER INFORMATION: b = nonstandard nucleotide of the invention
<220> FEATURE:
<221> NAME/KEY: misc_feature
<222> LOCATION: (7)..(7)
<223> OTHER INFORMATION: s = nonstandard nucleotide of the invention
<220> FEATURE:
<221> NAME/KEY: misc_feature
<222> LOCATION: (13)..(13)
<223> OTHER INFORMATION: b = nonstandard nucleotide of the invention
<220> FEATURE:
<221> NAME/KEY: misc_feature
<222> LOCATION: (46)..(46)
<223> OTHER INFORMATION: s = nonstandard nucleotide of the invention
<220> FEATURE:
<221> NAME/KEY: misc_feature
<222> LOCATION: (52)..(52)
<223> OTHER INFORMATION: b = nonstandard nucleotide of the invention
<220> FEATURE:

```
<221> NAME/KEY: misc_feature
<222> LOCATION: (55)..(55)
<223> OTHER INFORMATION: s = nonstandard nucleotide of the invention
<220> FEATURE:
<221> NAME/KEY: misc_feature
<222> LOCATION: (58)..(58)
<223> OTHER INFORMATION: b = nonstandard nucleotide of the invention

<400> SEQUENCE: 137
btcbagsgag aabtcaccat gagtgacgac tgaatccggt gagaasggca abagsttbt      59

<210> SEQ ID NO 138
<211> LENGTH: 44
<212> TYPE: DNA
<213> ORGANISM: Artificial Sequence
<220> FEATURE:
<223> OTHER INFORMATION: Synthesis
<220> FEATURE:
<221> NAME/KEY: misc_feature
<222> LOCATION: (2)..(2)
<223> OTHER INFORMATION: b = nonstandard nucleotide of the invention
<220> FEATURE:
<221> NAME/KEY: misc_feature
<222> LOCATION: (5)..(5)
<223> OTHER INFORMATION: b = nonstandard nucleotide of the invention
<220> FEATURE:
<221> NAME/KEY: misc_feature
<222> LOCATION: (14)..(14)
<223> OTHER INFORMATION: s = nonstandard nucleotide of the invention
<220> FEATURE:
<221> NAME/KEY: misc_feature
<222> LOCATION: (32)..(32)
<223> OTHER INFORMATION: s = nonstandard nucleotide of the invention
<220> FEATURE:
<221> NAME/KEY: misc_feature
<222> LOCATION: (41)..(41)
<223> OTHER INFORMATION: b = nonstandard nucleotide of the invention

<400> SEQUENCE: 138
cbagbtcctg gtascggtct gcgattccga cscgtccaac btca                      44

<210> SEQ ID NO 139
<211> LENGTH: 59
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: s = nonstandard nucleotide of the invention
<220> FEATURE:
<221> NAME/KEY: misc_feature
<222> LOCATION: (4)..(4)
<223> OTHER INFORMATION: b = nonstandard nucleotide of the invention
<220> FEATURE:
<221> NAME/KEY: misc_feature
<222> LOCATION: (10)..(10)
<223> OTHER INFORMATION: b = nonstandard nucleotide of the invention
<220> FEATURE:
<221> NAME/KEY: misc_feature
<222> LOCATION: (13)..(13)
<223> OTHER INFORMATION: b = nonstandard nucleotide of the invention
<220> FEATURE:
<221> NAME/KEY: misc_feature
<222> LOCATION: (46)..(46)
<223> OTHER INFORMATION: s = nonstandard nucleotide of the invention
<220> FEATURE:
<221> NAME/KEY: misc_feature
<222> LOCATION: (55)..(55)
<223> OTHER INFORMATION: s = nonstandard nucleotide of the invention
<220> FEATURE:
```

```
<221> NAME/KEY: misc_feature
<222> LOCATION: (58)..(58)
<223> OTHER INFORMATION: b = nonstandard nucleotide of the invention

<400> SEQUENCE: 139
sttbttcatb tcbggattat caataccata tttttgaaaa agccgsttct gtaasgabg    59

<210> SEQ ID NO 140
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: s = nonstandard nucleotide of the invention
<220> FEATURE:
<221> NAME/KEY: misc_feature
<222> LOCATION: (8)..(8)
<223> OTHER INFORMATION: s = nonstandard nucleotide of the invention
<220> FEATURE:
<221> NAME/KEY: misc_feature
<222> LOCATION: (11)..(11)
<223> OTHER INFORMATION: b = nonstandard nucleotide of the invention
<220> FEATURE:
<221> NAME/KEY: misc_feature
<222> LOCATION: (14)..(14)
<223> OTHER INFORMATION: s = nonstandard nucleotide of the invention
<220> FEATURE:
<221> NAME/KEY: misc_feature
<222> LOCATION: (34)..(34)
<223> OTHER INFORMATION: b = nonstandard nucleotide of the invention
<220> FEATURE:
<221> NAME/KEY: misc_feature
<222> LOCATION: (36)..(36)
<223> OTHER INFORMATION: s = nonstandard nucleotide of the invention
<220> FEATURE:
<221> NAME/KEY: misc_feature
<222> LOCATION: (39)..(39)
<223> OTHER INFORMATION: s = nonstandard nucleotide of the invention

<400> SEQUENCE: 140
ctagsggscg btcsgtccgt cctgtcagct gctbgscgsg cg    42
```

IN VIVO CONVERSION OF NUCLEOSIDES IN PLASMID DNA

CROSS REFERENCE TO RELATED APPLICATIONS

Figure 1:
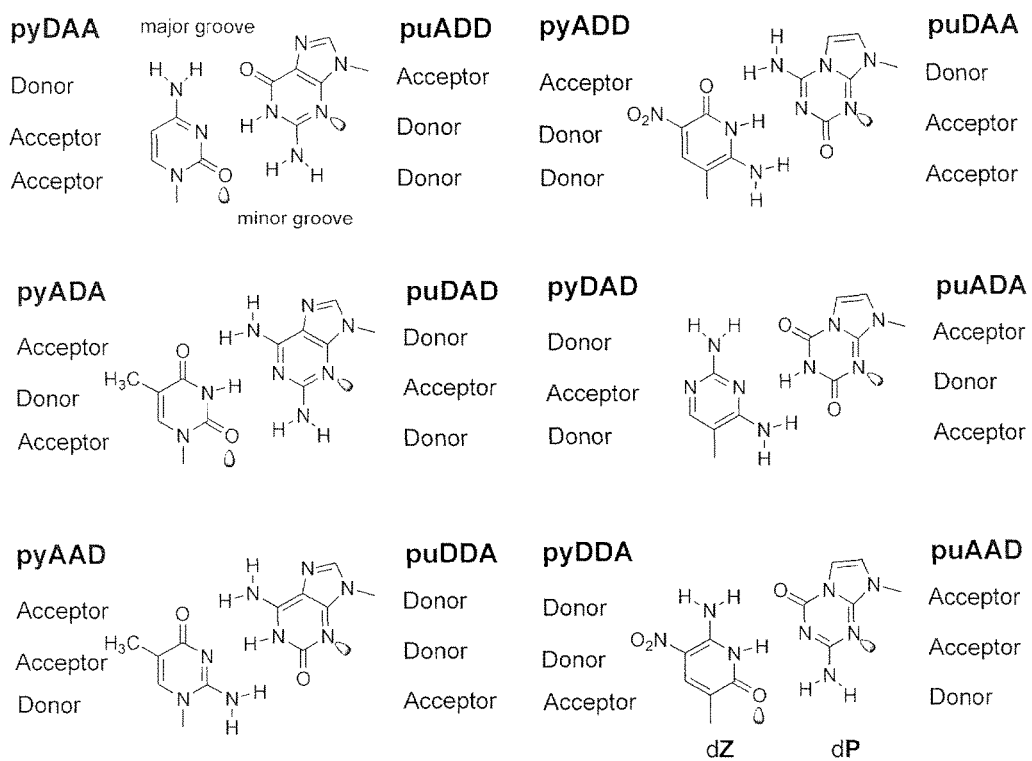

This Application claims benefit of U.S. Provisional Patent Application 61/802,913, filed Mar. 18, 2013, the disclosures of which are hereby incorporated by reference in their entirety, including all figures, tables and sequences. This Application claims priority to U.S. patent application Ser. No. 12/653,613, filed Dec. 16, 2009, which claims in part priority to the patent application filed under the PCT (with the United States as the receiving entity) having the designation US2009-003595.

STATEMENT OF RIGHTS TO INVENTIONS MADE UNDER FEDERALLY-SPONSORED RESEARCH

This invention was made with government support under N66001-12-C-4019 awarded by the Defense Advanced Research Projects Agency. The government has certain rights in the invention.

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION

(1) Field of the Invention

The field of this invention is nucleic acids and their analogs, and to processes that manipulate DNA, specifically the construction of DNA molecules by the assembly of smaller fragments of DNA by hybridization and, optionally, polymerase extension and/or ligation. Separately, the field of this invention also comprises nucleotide analogs that can form non-standard Watson-Crick nucleobase pairs that have similar geometry as standard Watson-Crick pairs, but are joined by a non-standard hydrogen bonding schemes. More specifically, this invention relates to processes that allow the assembly of multiple small fragments of DNA based on the hybridization of segments containing one or more non-standard nucleotides. More specifically, this invention relates to processes that then replace any non-standard nucleotides by more than one standard nucleotide. Most specifically, this invention relates to processes whereby that replacement occurs in living bacterial cells.

(2) Description of Related Art

Natural oligonucleotides bind to complementary oligonucleotides according to Watson and Crick rules of nucleobase pairing, where adenine (A) (or 2-aminoadenine) pairs with thymine (T) (or uracil, U), and guanine (G) pairs with cytosine (C), with complementary strands anti-parallel to one another. In this disclosure, "DNA" or "nucleic acid" is understood to include, as appropriate, both DNA (where the sugar is 2'-deoxyribose) and RNA (where the sugar is ribose), the 2'-O-alkyl and allyl derivatives, and these nucleic acids and their analogs in non-linear topologies, including dendrimers, comb-structures, and nanostructures, and these nucleic acids and their analogs carrying tags (e.g., fluorescent, functionalized, or binding) to the ends, sugars, or nucleobases, and/or non-nucleotidic material attached to the ends of the strand.

These pairing rules, which are largely context free and which can be applied without undue experimentation even by high school students, allow specific hybridization of an oligonucleotide to a complementary oligonucleotide, making oligonucleotides valuable as probes in the laboratory, in diagnostics, as messages that can direct the synthesis of specific proteins, and in other applications well known in the art. Such base pairing is used, as an example and without limitation, to capture other oligonucleotides to beads, arrays, and other solid supports, in linear and dendrimeric structures, to allow nucleic acids to fold in hairpins, beacons, and catalysts, as supports for functionality, such as fluorescence, fluorescence quenching, binding/capture tags, and catalytic functionality, as part of more complex architectures, including dendrimers and nanostructures, and as scaffolds to guide chemical reactions.

Further, nucleobase pairing is used by enzymes to catalyze the synthesis of new oligonucleotides that are complementary to template nucleotides. In this synthesis, building blocks (normally the triphosphates of ribo- or deoxyribonucleosides carrying of A, T, U, C, or G) are directed by a template oligonucleotide to form a complementary oligonucleotide with the complementary sequence. This serves as the basis for technologies for enzymatic synthesis and amplification of specific nucleic acids by enzymes such as DNA and RNA polymerase, in the polymerase chain reaction (PCR), and in a variety of architectures that may involve synthesis, ligation, cleavage, immobilization and release, inter alia, used in technology to detect nucleic acids.

The Watson-Crick pairing rules can be understood chemically as a consequence of the arrangement of hydrogen bonding groups on the heterocyclic nucleobases of the oligonucleotide, groups that can either be hydrogen bond donors or acceptors. In the standard Watson-Crick geometry, a large purine nucleobase pairs with a small pyrimidine nucleobase. Thus, the AT nucleobase pair is the same size as a GC nucleobase pair; the rungs of the DNA ladder, formed from either AT or GC nucleobase pairs, all have the same length. In this disclosure, to be "complementary in the Watson-Crick sense" means to have the Watson-Crick geometry, a full pairing (not wobble pairing) of a large purine and a small pyrimidine held together by three hydrogen bonds, or (if context demands) two hydrogen bonds, where in pairing is said to be "against" the nucleotide in the complementary strand, in an antiparallel orientation, to which it is matched.

The specificity of recognition between large and small nucleobases is determined by hydrogen bonding between the nucleobases. In standard nucleobases, hydrogen bond donors are heteroatoms (nitrogen or oxygen in the natural nucleobases) bearing a hydrogen, while hydrogen bond acceptors are heteroatoms (nitrogen or oxygen in the natural nucleobases) with a lone pair of electrons. In the Watson-Crick nucleobase pairing geometry, a six membered ring (in standard nucleobases, a pyrimidine) pairs with a ring system composed of a fused five-six ring system (in standard nucleobases, a purine), with a middle hydrogen bond linking two ring atoms, and hydrogen bonds on either side joining functional groups appended to each of the rings, with donor groups paired with acceptor groups. The AT nucleobase pair uses this hydrogen bonding pattern only partly; it is completely used in the diaminoA:T base pair.

In 1990, the instant Inventor filed the first patent application (which later issued as U.S. Pat. No. 5,432,272) disclosing compositions of matter that expanded the number of nucleobases that could pair by such simple rules. He proposed eight additional nucleobases that form four additional pairs by changing the pattern of hydrogen bond donor and acceptor groups presented by a nucleobase to the nucleobase on a complementary oligonucleotide analog [U.S. Pat. Nos. 5,432,272, 5,965,364, 6,001,983, 6,037,120, 6,140,496, 6,627,456, 6,617,106]. These disclosures showed that the geometry of the Watson-Crick nucleobase pair could accommodate as many as 12 nucleobases forming 6 mutually exclusive pairs. Of these, four nucleobases forming two pairs are "standard", while eight nucleobases forming four pairs were termed "non-standard". Adding the non-standard nucleobases to the standard nucleobases yielded an Artificially Expanded Genetic Information System (AEGIS). It was also noted that these nucleobases analogs might be functionalized to enable a single biopolymer capable of both genetics and catalysis.

Expanded genetic alphabets have now been explored in many laboratories, and the possibility of a fully artificial genetic system has been advanced [Swi89][Pic90] [Pic91] [Voe93] [von95] [Voe96a] [Voe96b] [Kod97] [Jur98] [Lut99] [Jur99] [Jur00], the contents of which are incorporated by reference.

To systematize the nomenclature for the hydrogen bonding patterns, the hydrogen bonding pattern implemented on a small component of a nucleobase pair are designated by the prefix "py". Following this prefix is the order, from the major groove to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Again following the prefix, the hydrogen bond donor and acceptor groups are designated, from the major to the minor grooves, using "A" and "D". Thus, the standard nucleobases adenine and guanine implement the standard hydrogen bonding patterns puDA- and puADD respectively.

A teaching of this disclosure is that hydrogen-bonding patterns designated using this systematic nomenclature are distinct in concept from the organic molecules that are used to implement the hydrogen-bonding patterns. Thus, guanosine is a nucleoside that implements the puADD hydrogen-bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups. Which organic molecule is chosen to implement a specific hydrogen-bonding pattern determines, in large part, the utility of the non-standard hydrogen-bonding pattern, in various applications to which it might be applied.

The additional nucleobase pairs, because of their desirable pairing properties, chemical stability, and other features known to those skilled in they art, have been useful for a variety of purposes. For example, the nucleobase pair between 2-amino-5-methyl-1-(1'-beta-D-2'-deoxyribofuranosyl)-4(1H)-pyrimidine, also known as 2'-deoxyisocytidine, disoC, or sometimes (less correctly) isoC and implementing the pyAAD hydrogen bonding pattern, and 6-amino-1,9-dihydro-9-(1'-beta-D-2'-deoxyribofuranosyl)-3H-purin-2-one, also known as 2'-deoxyisoguanosine, disoG, or sometimes (less correctly) isoG, and implementing the puDDA hydrogen bonding pattern, is incorporated into the branched DNA diagnostics tools marketed today by Bayer and its successor, Siemens. Here, the non-standard nucleobase pair supports orthogonal molecular recognition in aqueous solution, similar to nucleic acids but with a coding system that is orthogonal to the system in DNA and RNA, Thus, it allows the assembly of the branched dendrimer in the assay free from inhibition by adventitious nucleic acid, and prevents adventitious nucleic acid from capturing signaling elements form the nanostructure in the absence of the target analyte nucleic acid, creating noise. Further, adding extra letters to the genetic alphabet speeds hybridization, presumably because it decreases the number of close mismatches where DNA dwells before finding its fully matched partner. The branched DNA assay has FDA-approval and is widely used to provide personalized patient care in the clinic.

One of the advantages of incorporating non-standard nucleotides into human diagnostic assays is that binding between oligonucleotides containing these can occur without interference from natural DNA, which is often present in abundance in samples taken from human tissues. Such binding is often used to concentrate samples from complex mixtures, on arrays or at the bottoms of plastic wells. Natural DNA, built from A, T, G, and C, will interfere with A:T and G:C interactions. This leads to large amounts of noise in DNA arrays, for example. Accordingly, in the branched DNA assays, non-standard nucleotides are incorporated by chemical synthesis into the portion of tags that are used to move the analyte to a spot where it can be detected and to assemble signaling dendrimers.

Pairing between non-standard nucleotides cannot be used to directly bind natural analytes, as these analytes are themselves built from A, T, G, and C. Accordingly, when non-standard nucleotides are used to achieve orthogonality in clinical diagnostic assays [Elb04a][Elb04b], they are general appended as tags to primary probes, which are built from A, T. G, and C. The primary probes are the ones that contact the analyte targeted by the diagnostic assay. This limits considerably the use of non-standard components to achieve orthogonality and high signal-to-noise ratios in biological systems. A process that creates replicates or complements of oligonucleotides that replace in a controlled fashion standard nucleotides by non-standard nucleotides would therefore have utility. If this is sequence specific, the pairing of the resulting replicate or complement through non-standard base pairs could, in an appropriate architecture, offer an element of selectivity for the analyte in addition to those selectivity elements based on other regions of the analyte (for example, the regions that bind PCR amplification primers).

Conversely, oligonucleotides containing non-standard nucleotides cannot today be introduced into standard cloning systems. No strain used for cloning, including *E. coli* strains, is known to have the cellular machinery for making the triphosphates of non-standard nucleosides and using them to replicate DNA containing non-standard nucleotides. A process that creates replicates or complements of oligonucleotides that replace in a controlled fashion non-standard nucleotides by standard nucleotides (a vice versa process) would therefore have utility. Further, such a process would most useful if it is a process pair, where the product from one process replaces the non-standard nucleotide by one standard nucleotide, and another replaces the non-standard nucleotide by a different standard nucleotide. This makes it possible to compare the sequences of the two resulting replicates or complements to ascertain where in the oligonucleotide sequence the original non-standard nucleotide(s) was (were) found.

Mismatching is known between non-standard and standard pairs such that a standard nucleotide is incorporated opposite a nonstandard nucleotide in the template. For example, Sepiol et al. [Sep76] recognized that isoG, which presents a hydrogen bond donor-donor-acceptor pattern complementary to the acceptor-acceptor-donor pattern of isoC, exists in water to about 10% as an enol tautomeric form, which can present a hydrogen bond donor-acceptor-donor hydrogen bonding pattern complementary to T (acceptor-donor-acceptor). Work in the 1990's showed that polymerases of various types would incorporate T (or U) opposite isoG in a template, presumably by pairing between T (or U) and the minor tautomeric form of isoG [Swi93]. This caused the loss of the isoG:isoC pair in (for example) PCR reactions [Joh04], a loss that was considered throughout the art to be disadvantageous, as it appeared to deprive the product from the possibility of the PCR product of having the orthogonal isoC:isoG pair.

Struggling to suppress this mispairing between T and the minor tautomeric form of isoG, the instant Inventor and Michael Sismour exploited the discovery that the minor tautomer of isoG does not pair well with 2-thio, and replaced T with 2-thioT in a polymerase incubation [Sis05]. Therefore, products derived from a six letter PCR incorporating A, G, C, 2-thioT, isoG and isoC was able to retain the isoC and isoG non-standard components after many more cycles than a six letter PCR where standard T was used instead of 2-thioT. Thus, the products were able to retain the ability to be orthogonally bound by isoG:isoC pairing after many more cycles of PCR. Further attempting to avoid mispairing and isoG:T (or U) mismatching, 7-deazaisoG was developed [Mar04].

These examples from the prior art show the extent to which those in the art view as undesirable the mismatching between standard nucleotides and non-standard nucleotides, and thereby teach away from the instant invention, which is based on an inventive step that recognizes the utility of mismatching.

BRIEF SUMMARY OF THE INVENTION

This invention is based on an unexpected discovery that when plasmid DNA containing base pairs between the nucleotides Z and P, or between the nucleotides S and B (as defined in FIG. 1), when introduced as a vector into *E. coli*, leads to a plasmid where the non-standard nucleotides are not lost by deletion, but rather are converted into standard nucleotides with substantial control over the replacement, with Z:P largely being replaced by C:G, and S:B being largely replaced by T:A. As a further discovery, the rules governing the replacement are different in strains of *E. coli* lacking the mut S gene.

BRIEF DESCRIPTION OF THE SEVERAL VIEWS OF THE DRAWING(S)

FIG. 1. One example of an "artificially expanded genetic information system" (AEGIS). Nucleobase pairs in this system have a Watson-Crick geometry, with large purines or purine analogs (indicated by "pu") pairing with small pyrimidines or pyrimidine analogs (indicated by "py") joined by hydrogen bonds. The hydrogen-bonding acceptor (A) and donor (D) groups are listed from the major to the minor groove as indicated. The heterocycles shown are the currently preferred implementations of the indicated hydrogen bonding patterns; others are conceivable. Electron density presented to the minor groove is shown by the shaded lobes. Note that some non-standard pyrimidines do not present this density. The nucleotides implementing the pyDDA:puAAD hydrogen bonding pattern, the topic of this paper, are at the bottom right.

Figure 2:
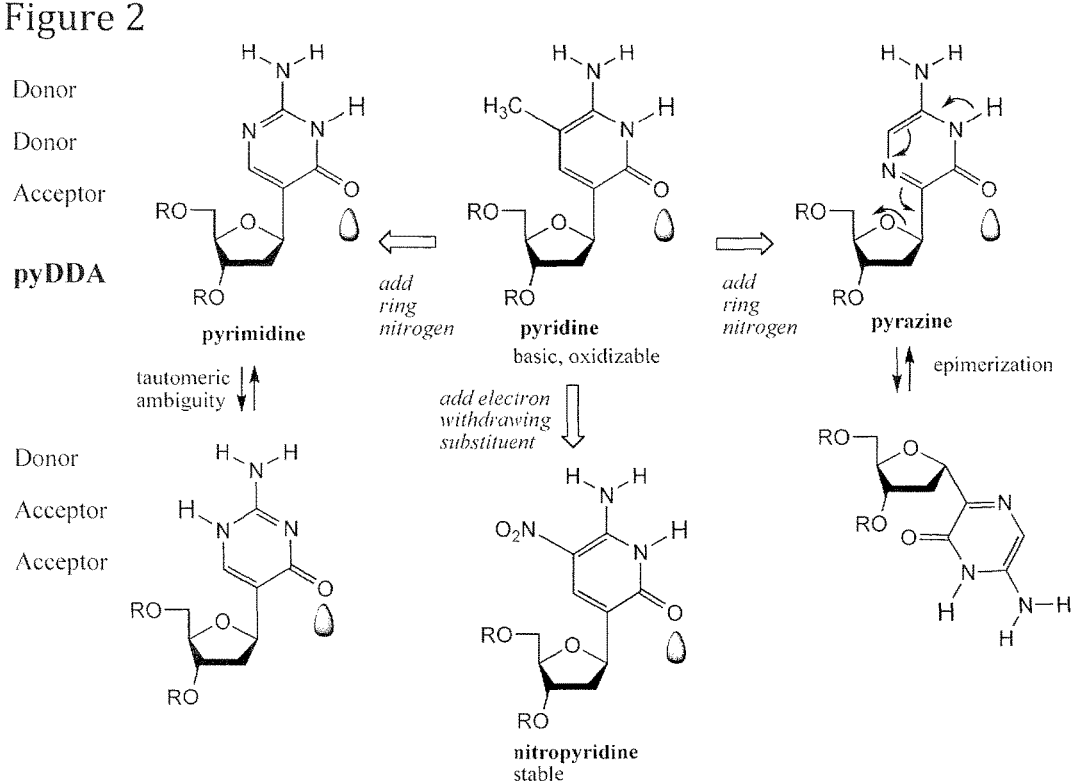

FIG. 2. Four alternative implementations of the pyDDA hydrogen bonding pattern. The implementation on a pyrimidine heterocycle suffers from tautomeric ambiguity (left). The implementation on a pyrazine suffers from facile epimerization (right). The implementation on a simple pyridine is too basic and prone to oxidation (top center). The preferred implementation is the nitropyridine heterocycle (discussed here, bottom center), which is stable to oxidation, is not basic, and does not epimerize near neutral pH.

Figure 3:
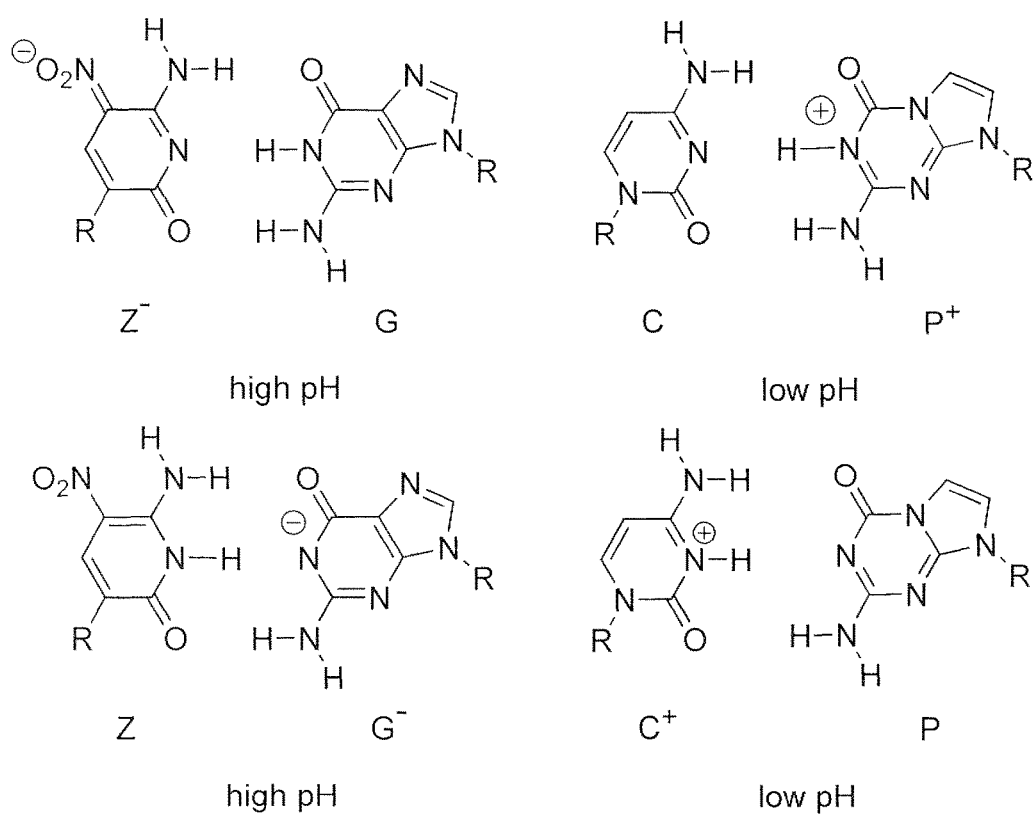

FIG. 3. Nucleobases structured to place non-standard nucleotides in a polymerase-generated product opposite specific standard nucleotides using protonated and deprotonated forms.

Figure 4:
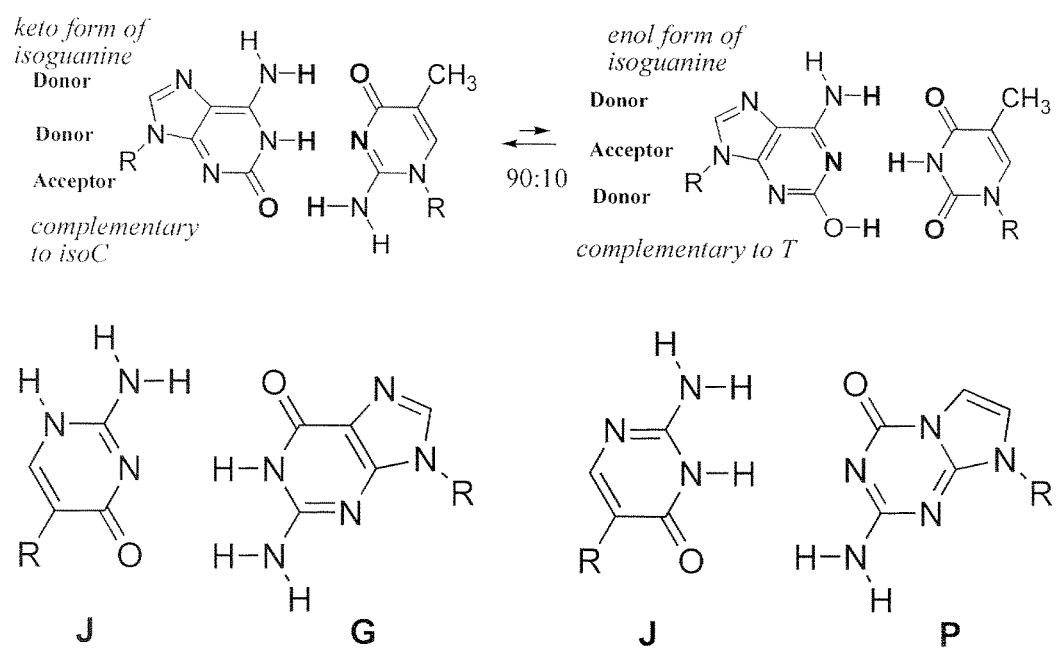

FIG. 4. Nucleobases structured to place non-standard nucleotides in a polymerase-generated product opposite specific standard nucleotides by virtue of their having tautomeric forms.

Figure 5:
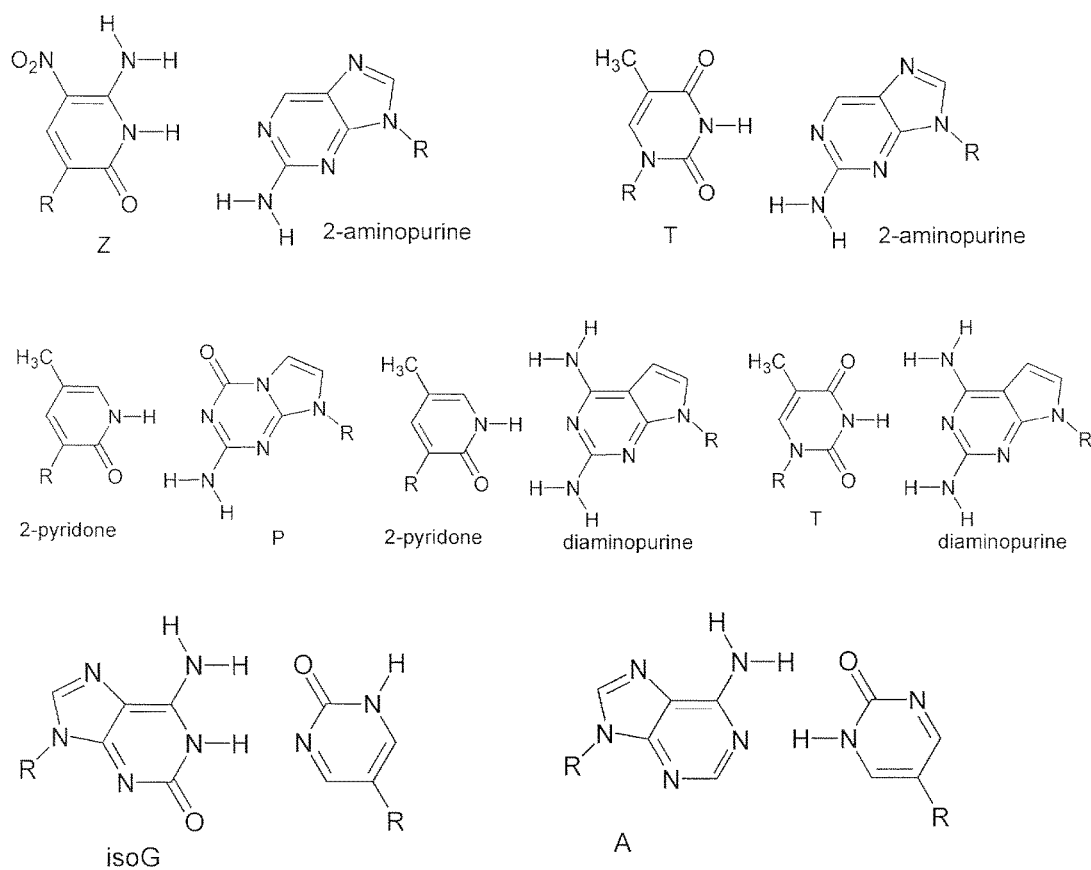

FIG. 5. Nucleobases structured to place non-standard nucleotides in a polymerase-generated product opposite specific standard nucleotides exploiting a nucleobase that presents two hydrogen bond that a standard and non-standard base have in common.

Figure 6:
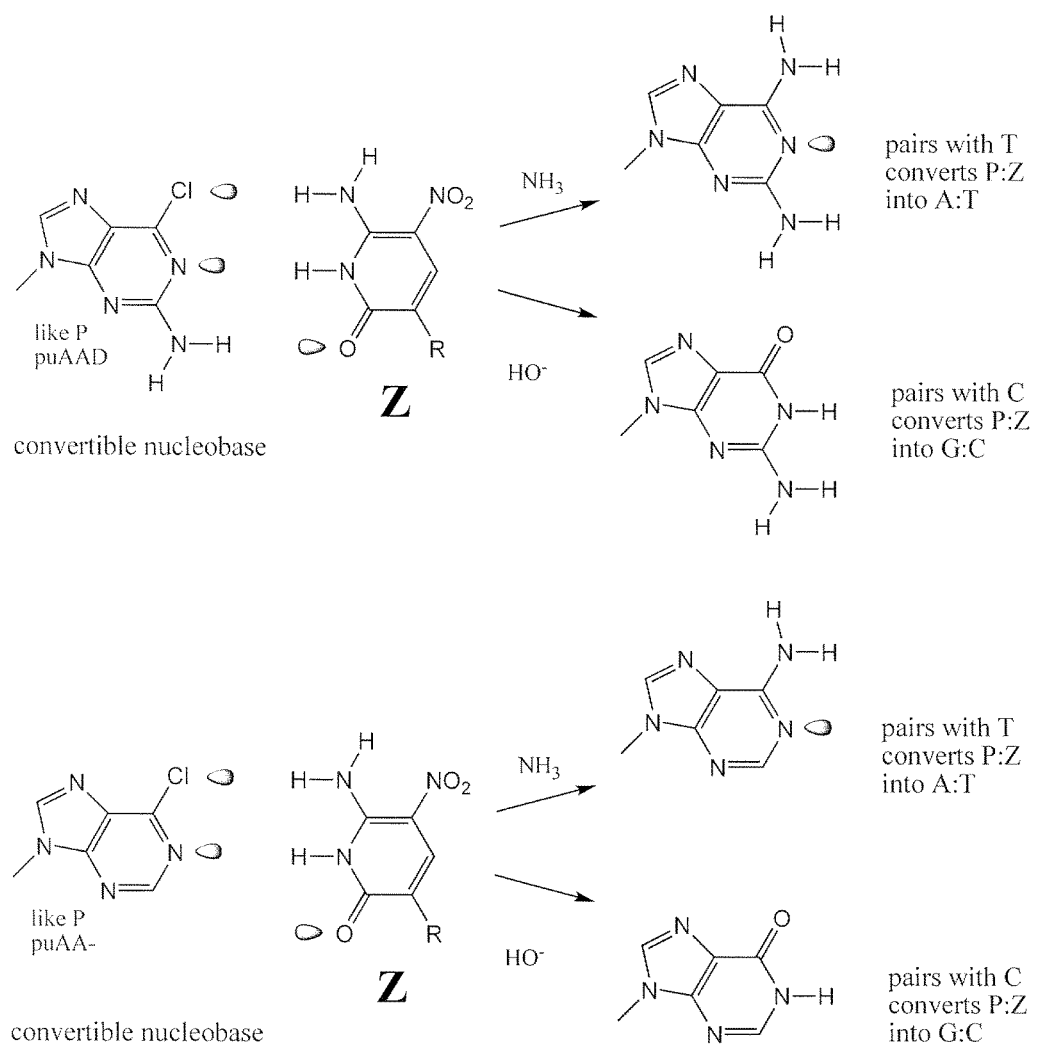

FIG. 6. Nucleobases structured to place standard nucleotides in a polymerase-generated product opposite specific non-standard nucleotides exploiting a nucleobase that complements the non-standard base that, upon subsequent treatment with chemical reagents, can generate two different standard nucleobases. This allows the products to be cloned, and further allows one to compare the sequences in the cloned products to decide where the non-standard nucleotides originally were.

Figure 7:
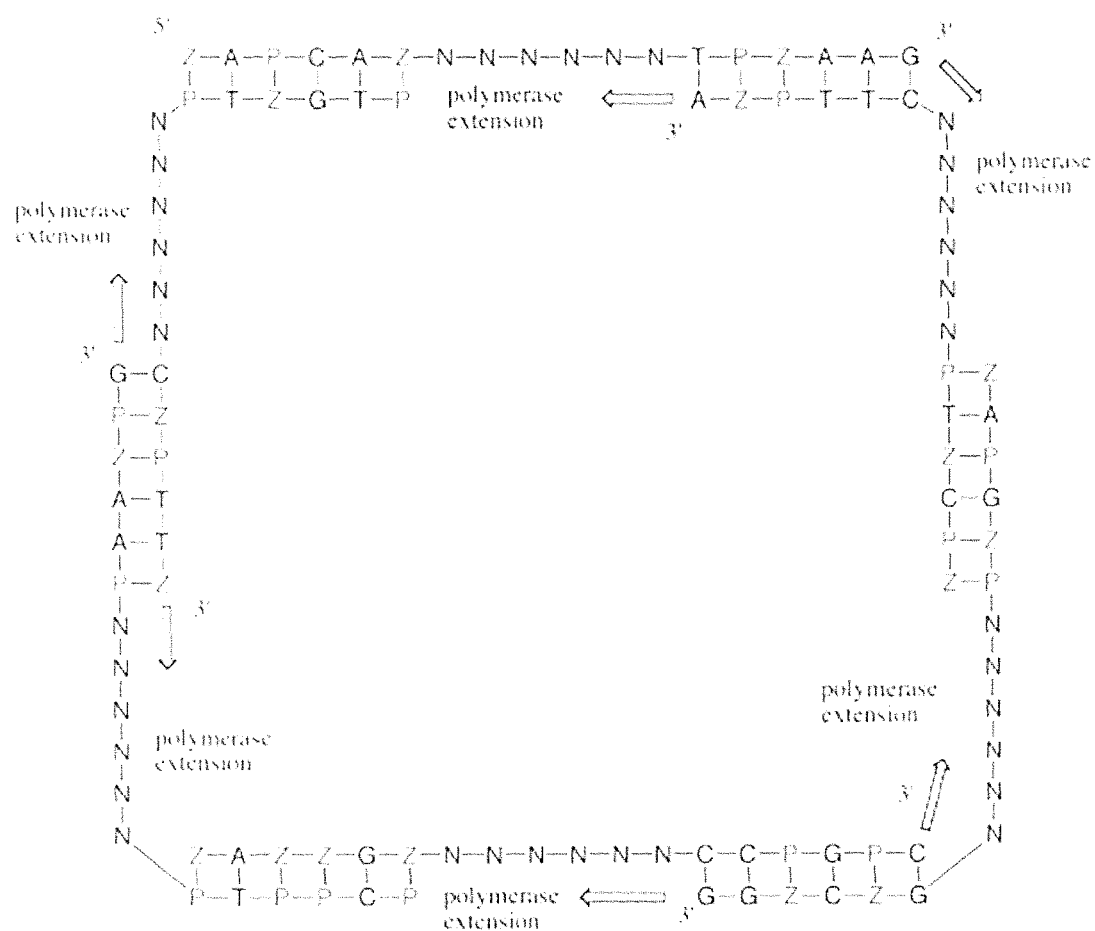
Figure 8:
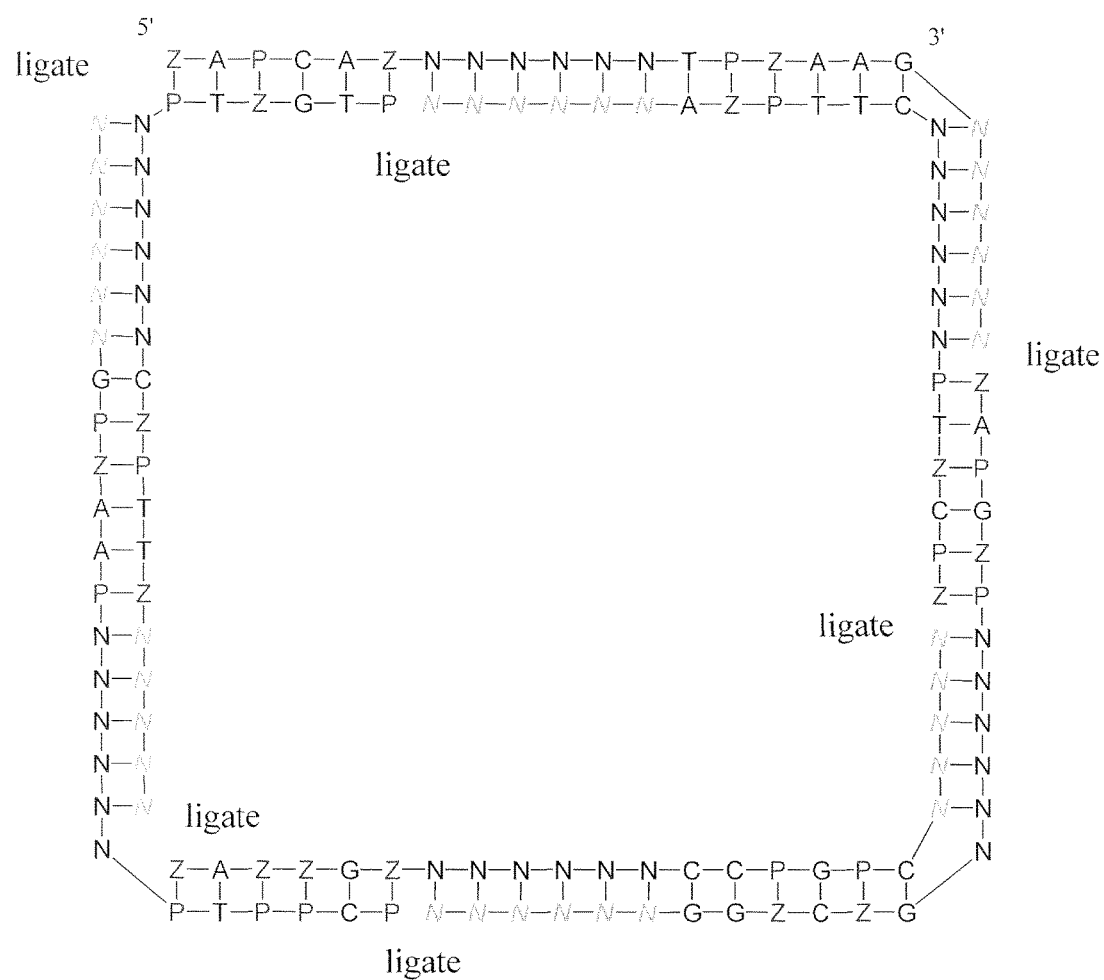

FIG. 7. Schematic of a procedure to create DNA constructs that exploits (a) an increased number of independently pairing nucleotides in synthetic DNA, (b) the orthogonality of pairing between these to allow the synthetic biologists more control over the assembly of synthetic DNA fragments, and (c) strains of *E. coli* that accept DNA constructs containing additional, artificial nucleotides, convert the artificial base pairs to standard base pairs, and delivers a final, entirely FIG. 8. Schematic of a procedure to create DNA constructs includes polymerase extension and ligation.

Figure 9:
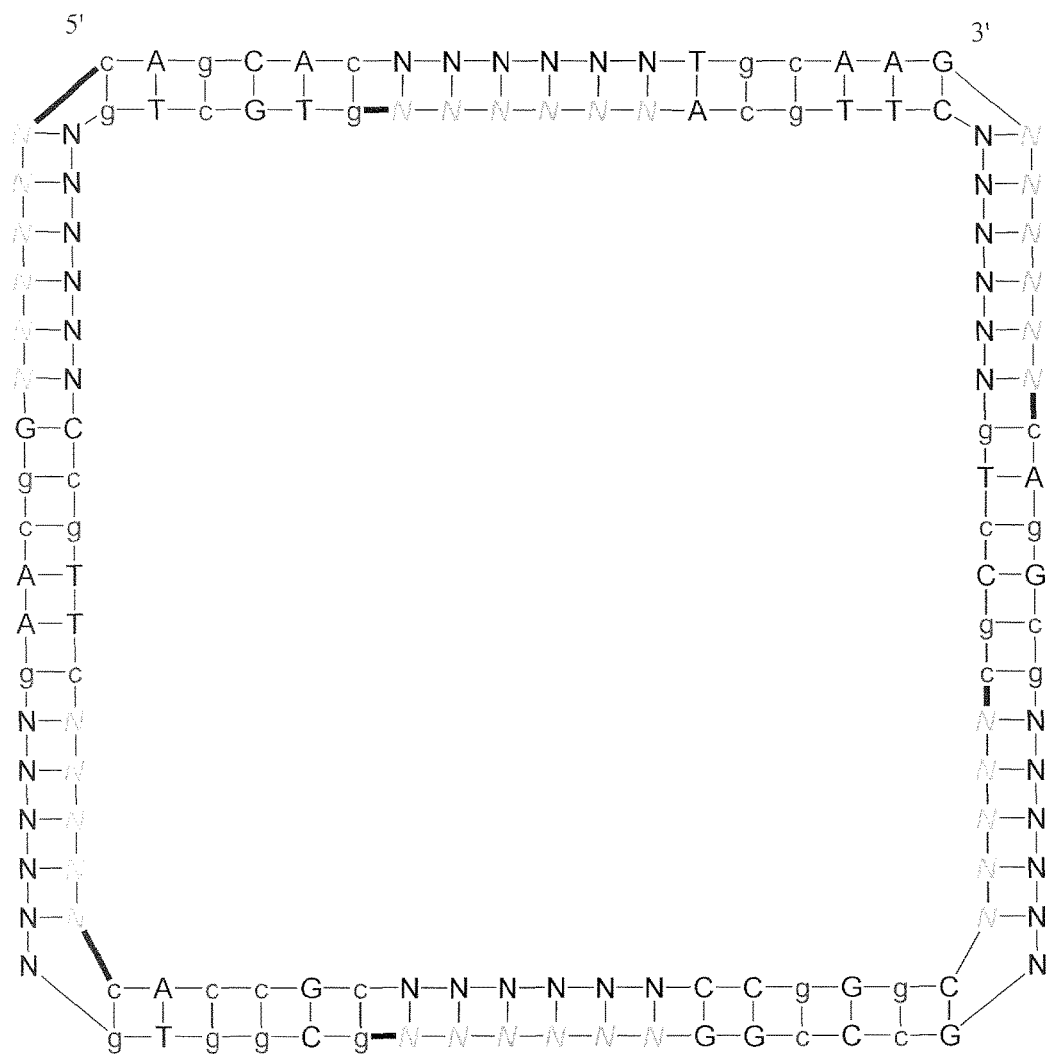

FIG. 9. Schematic of a procedure to create DNA constructs includes polymerase extension and ligation, after conversion according to the instant invention.

Figure 10:
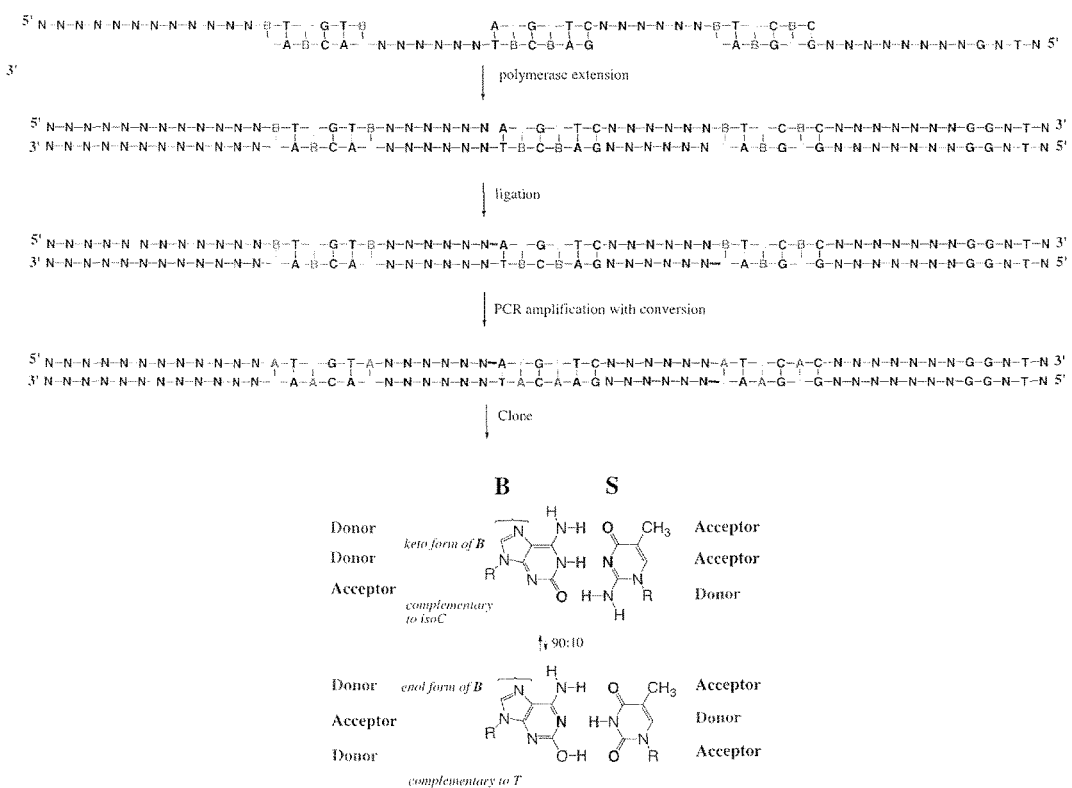

FIG. 10. Schematic showing the mix-anneal-extend-ligate-amplify processes. The process starts by mixing single stranded DNA fragments designed to have their ends anneal as duplexes that include S:B pairs (note the colors). The higher information density enabled by the additional S:B pair lowers off-target hybridization, eliminates hairpins, and better guides the formation of the desired duplexes. After these duplexes are formed, the 3'-ends are extended using a polymerase that does not displace strands to give nicked DNA. Ligase then seals the nicks by forming the red bonds. Then, PCR amplification with conversion (shown here) or direct transformation into Firebug™ replaces the S:B pairs in the construct by T:A pairs. The conversion is mediated by polymerases that incorporate T opposite the enol form of B, a minor tautomer that presents the donor-acceptor-donor hydrogen bonding pattern complementary to the acceptor-donor-acceptor hydrogen bonding pattern presented by T. Thus, after two cycles of PCR, template B has be been replaced by A via an intermediate B:T misparing, while template S has be been replaced by T via an intermediate S:B pairing followed by a second intermediate B:T misparing.

DETAILED DESCRIPTION OF THE INVENTION

The presently preferred method for practicing the instant invention assembles four or more DNA oligonucleotide fragments following the schematic shown in FIG. 10. Here, each internal fragment (that is, a fragment that will not end up at the end of the construct) has three regions:

(i) A region (the 5'-hybridizing region) at its 5'-end that can hybridize to the 5'-end of another fragment.

(ii) A region (the 3'-hybridizing region) at its 3'-end that can hybridize to the 3'-end of another fragment.

(iii) Optionally, a third region between the 5'-hybridizing region and the 3'-hybridizing region that does not hybridize to any other region.

The end fragments (should the target construct be linear, rather than circular) lack one or the other of these hybridizing regions. Thus, the 5'-end of the linear construct will have a 3'-hybridizing region, but not a 5'-hybridizing region. Alternatively, the ends might be made in blunt end duplex form. The details of the end assembly are not critical to the inventive portions of this invention.

Annealing of the fragments yields a concatamer, where the 3'-hybridizing region of the first (5'-end) top strand (making reference to FIG. 10) hybridizes to the 3'-hybridizing region of the last (3'-end) bottom strand. Then, the 5'-hybridizing region of the last bottom strand hybridizes to the 5'-hybridizing region of the second top strand. Further bottom and top strands then can anneal to form a complete concatamer.

The schematic in FIG. 10 shows third regions (the 6 consecutive Ns) that are not hybridized in the concatamer. If the 5'-hybridizing regions and 3'-hybridizing regions are long enough, these third regions need not exist. The concatamer can therefore be instantly assembled by ligation using an enzyme ligase. If unhybridized third regions exists in the concatamer, these can be filled in by a DNA polymerase that does not do strand displacement. The filled in product can then have its nicks ligated, to give the full length product, the desired target construct.

As described, this assembly is neither novel nor inventive. The inventive component arises from the use of non-standard nucleotides to assist the assembly. In the schematic shown in FIG. 10, the non-standard nucleotides S and B are placed in the 3'- and 5'-hybridizing regions. The specific sequences of these regions are designed to ensure that the hybridization using Watson-Crick pairing rules expanded to include non-standard nucleobase pairs. This increases the information density in the fragments overall, ensuring the correct assembly of the fragments. Further, the non-standard nucleotides are, by design, placed at sites where, after conversion, the standard nucleotide desired in the construct is created.

The S:B pair is most presently preferred; the Z:P pair is also presently preferred. Other pairs are possible according to conversion rules known in the art.

Thus, the inventive step involves the used of extra non-standard nucleotides to increase the information density of the fragments as they are assembled via annealing to give a concatamer. Also inventive is the conversion of non-standard nucleotides, after their value in directed assembly is used, to standard nucleotides. This is done by the final process, which is the copying of the ligated construct by a DNA polymerase that performs the conversion. This can be done in vivo, in *E. coli*, where the design ensures that the rules of conversion yield, after conversion, the sequence that is desired in the final target construct. These are shown in Example 1.

Conversion can be done in vitro, using conditions that provide rule-based conversions. Example 2 shows this conversion with S:B as the non-standard pair, with the conversion replacing S:B pairs in the initial ligated construct by T:A pairs in the final construct.

EXAMPLES

Example 1

Rules for conversion of Z:P pairs to C:G pairs in living *E. coli*

TABLE 1 inserts designed and synthesized from phosphoramidites of Z, P, S and B.

5'-(P)CATGT CTGATCCTGCACTGCTGGGCCCTTGACTCTCGTACC TG-3' (3Dm-1PZ) SEQ ID NO. 1

3' A GACTAGGACGTGACGACCCGGGAACTGAGAGCATGGAC TCG (P)-5' (3dNK-1ZP) SEQ ID NO. 2

5'-(P)CATG TCaacTCCTGCgtgcGGCCTTGACTCTCGTACCTG-3' (Control insert Top3) SEQ ID NO. 3

3'-AGttgAGGACGcacgCCGGAACTGAGAGCATGGAC TCG(P)-5' (Control insert Bot3) SEQ ID NO. 4

5'-(P)CATG TCaaZTCCTGCPtPZGGCCTTGACTCTCGTACCTG-3' (EcoK1-ZP Top1) SEQ ID NO. 5

3'-AGttPAGGACGZaZPCCGGAACTGAGAGCATGGAC TCG(P)-5' (EcoK1-ZP Bot1) SEQ ID NO. 6

5'-(P)CATG TCaaZTZZTPZPtPZPPZZTTGACTCTCGTACCTG-3' (EcoK1-ZP Top2) SEQ ID NO. 7

3'-AGttPAPPAZPZaZPZZPPAACTGAGAGCATGGAC TCG(P)-5' (EcoK1-ZP Bot2) SEQ ID NO. 8

Ligations were set up following the recipe in Table 2. Prior to dilution, inserts were annealed at equal molar ratios in 7.5 mM Tris-HCl pH 7.5, 50 mM KCl, and 0.5 mM EDTA (referred to as DNA annealing buffer) by heating to 94° C. for min followed by a 10 min ramp down to room temperature on a thermocycler. Inserts were then diluted to a working concentration of 5 µM. Ligations were set up on a cold block and then transferred to 16° C. incubation for at least an hour.

TABLE 2

Ligation p15a + Insert Dec. 14, 2010 All reaction volumes total = 20 µL.

| Component | [initial] | Reagents (µL) | [final] | # of molecules |
|---|---|---|---|---|
| dd H$_2$O | | 10.7 | | |
| lig/gyr buffer | 5 | 4 | 1 | |
| Insert (µM) | 5 | 3.00 | 0.75 | 4.533E+12 |
| Vector (ng/µL) | 150 | 1.33 | 10 | 6.01E+10 |
| DTT (mM) | 500 | 0.40 | 10 | |
| ATP (mM) | 50 | 0.40 | 1 | |
| Enzyme Units/µl | 400 | 0.2 | 4 | insert: vector |
| | | 20 | | 75.44 |

Transformations were done into chemically competent DH5α cells from Invitrogen. The first transformation of inserts containing 1 ZP pair gave fewer clones than the control. However, after insert concentration was and corrected, the number of clones generated were similar with plasmids containing one or two Z:P pairs or 2 gave roughly the same amount of clones.

To confirm the presence of insert in the clones, colony PCR was performed on 22 clones from the 1 Z:P pair set and two clones from the control insert set. A diagnostic primer ID-F3 anneals entirely within the insert after the Z:P pairs and forms a 350 bp product with the ID-R1 primer if insert is present. Twenty-one clones contained insert in this set and all 12 of the two Z:P pair set tested also contained insert. Thus background re-circularization of the vector is negligible, indicating that almost all the clones have insert. The equivalent transformation efficiencies of control and ZP containing DNA along with the presence of insert in almost all clones indicates that the ZP pairs have negligible toxicity to the bacteria.

To determine the fate of the Z:P pairs, six clones from each set (designated 1ZP and 2ZP) were cultured, and plasmid was recovered and sequenced. The sequencing primer was the ID-R1 which anneals to the bottom (or negative) strand so to compare them to the insert the inverse complement of the insert must be created so the sequences align. All the sequences were good quality with no rearrangements within or outside of the insert. To simplify the visualization of the base substitutions, the NCBI align program to create the difference matrix below. A period indicates identical base and dash indicates a 1 nt deletion. The target site is underlined; this site contained P in the original plasmid.

TABLE 3

Sequences following conversion in vivo in E. coli (mutS+)

```
Query  301  AGTCAAPPGCCCAGCAGTGCAGGATCAGACATGTCCTGAACCGACGACCGGGTCGAATTT  360
SEQ ID NO. 9

1Z-1   301  ......GG....................................................  360
SEQ ID NO. 10

1Z-2   301  ......AG....................................................  360
SEQ ID NO. 11

1Z-3   301  ......AG....................................................  360
SEQ ID NO. 11

1Z-4   301  ...-..AG....................................................  359
SEQ ID NO. 12

1Z-5   301  ......GG....................................................  360
SEQ ID NO. 10

1Z-6   302  ......GG....................................................  361
SEQ ID NO. 13

2Z-1   301  ......GG....................................................  360
SEQ ID NO. 10

2Z-2   301  ......GG....................................................  360
SEQ ID NO. 10

2Z-6   301  ......GG....................................................  360
SEQ ID NO. 10

2Z-7   302  ......GG....................................................  361
SEQ ID NO. 13

2Z-8   311  ......GG....................................................  370
SEQ ID NO. 14
```

Through the data collected, only transitions, and never transversions, were observed.

TABLE 4

Sequences following conversion in vivo in *E. coli* (mutS+)

```
K1-PZ set              CATGTCaaCTCCTGCGtPZGGCCTTGACTCTCGTACCT
SEQ ID NO. 15

Query    119   CGACCCGGTCGTCGGTTCAGGACATGTCAACTCCTGCGTGCGGCCTTGACTCTCGTACCT  178
SEQ ID NO. 16

PZ-1_SEQ-F2-A1  .......................................AC..................  171
SEQ ID NO. 17
```

TABLE 4-continued

Sequences following conversion in vivo in E. coli (mutS+)

```
PZ-1_p15a-R2-A1     ........................................AC................... 358
SEQ ID NO. 18

PZ-2_SEQ-F2-A2      ........................................AC................... 170
SEQ ID NO. 19

PZ-2_p15a-R2-A2     ........................................AC................... 358
SEQ ID NO. 20

PZ-3_SEQ-F2-A3      ........................................AC................... 169
SEQ ID NO. 21

PZ-4_SEQ-F2-A4      ........................................GT................... 171
SEQ ID NO. 22

PZ-6_SEQ-F2-A6      ........................................AC..................- 169
SEQ ID NO. 23

PZ-7_SEQ-F2-A7      ........................................GT................... 169
SEQ ID NO. 24

PZ-8_SEQ-F2-A8      ........................................AC................... 184
SEQ ID NO. 25

PZ-9_SEQ-F2-A9      ........................................AC................... 173
SEQ ID NO. 26

PZ-10_SEQ-F2-A10    ........................................AC................... 171
SEQ ID NO. 27

PZ-11_SEQ-F2-A11    ........................................AC................... 469
SEQ ID NO. 28

PZ-12_SEQ-F2-A12    ........................................AC................... 171
SEQ ID NO. 29
```

PZ-5 lacked insert; 81% converted to AC

Substitution of PtP (always gives GTG) in DH5-alpha
Recomb (−) MutS (+)

TABLE 5

Sequences following conversion in vivo in E. coli (mutS+)

```
                    CATGTCaaCTCCTGCPtPCGGCCTTGACTCTCGTACCT
SEQ ID NO. 30
Query 119           CGACCCGGTCGTCGGTTCAGGACATGTCAACTCCTGCGTGCGGCCTTGACTCTCGTACCT 178
SEQ ID NO. 31
PtP-1_SEQ-F2-E9     CGACCCGGTCGTCGGTTCAGGACATGTCAACTCCTGCGTGCGGCCTTGACTCTCGTACCT 185
SEQ ID NO. 32

PtP-2_SEQ-F2-E10    .........................A...........G.G................... 171
SEQ ID NO. 33

PtP-3_SEQ-F2-E11    CGACCCGGTCGTCGGTTCAGGACATGTCAACTCCTGCGTGCGGCCTTGACTCTCGTACCT 173
SEQ ID NO. 34

PtP-4_SEQ-F2-E12    ....T.................................G.G................... 172
SEQ ID NO. 35

PtP-5_SEQ-F2-F1     ......................................G.G................... 174
Seq ID NO. 36

PtP-6_SEQ-F2-F2     ......................................G.G................... 171
SEQ ID NO. 37

PtP-7_SEQ-F2-F3     ......................................G.G................... 189
SEQ ID NO. 38

PtP-8_SEQ-F2-F4     ......................................G.G................... 178
SEQ ID NO. 39

PtP-9_SEQ-F2-F5     ......................................G.G................... 172
SEQ ID NO. 40
```

TABLE 5-continued

Sequences following conversion in vivo in E. coli (mutS+)

```
PtP-10_SEQ-F2-F6    ......................................G.G.............  167
SEQ ID NO. 41

PtP-11_SEQ-F2-F7    ......................................G.G.............  172
SEQ ID NO. 42

PtP-12_SEQ-F2-F8    ......................................G.G.............  184
SEQ ID NO. 43

PtP-13_SEQ-F2-F9    ......................................G.G.............  171
SEQ ID NO. 44

PtP-14_SEQ-F2-F10   ......................................G.G.............  172
SEQ ID NO. 45

PtP-15_SEQ-F2-F11   ..............A.........................G.G.............  171
SEQ ID NO. 46

PtP-16_SEQ-F2-F12   ......................................G.G.............  170
SEQ ID NO. 47

PtP-17_SEQ-F2-G1    ......................................................  174
SEQ ID NO. 48

PtP-18_SEQ-F2-G2    ......................................................  189
SEQ ID NO. 49

PtP-19_SEQ-F2-G3    ......................................................  188
SEQ ID NO. 50

PtP-20_SEQ-F2-G4    ......................................................  190
SEQ ID NO. 51
```

TABLE 6

Sequencing of converted P:Z inserts from STL13780 ΔmutS

| Data Set Name | Target Sequence | # of good sequences | P:Z to G:C | P:Z to A:T | Z:P to C:G | Z:P to T:A |
|---|---|---|---|---|---|---|
| 2Z | 5'-CZZT SEQ ID NO. 52 3'-gPPA SEQ ID NO. 53 | 11 | | | 10 | 0 (one deletion) |
| 2ZP | 5'-gPggCCZC SEQ ID NO. 54 3'-CZCCggPg SEQ ID NO. 54 | 12 | 5 | 7 | 9 | 3 |
| K1-PZ | 5'-TPZg SEQ ID NO. 55 3'-AZPC SEQ LD NO. 56 | 10 | 7 | 3 | 4 | 6 |
| K1-ZP | 5'-TZPg SEQ ID NO. 57 3'-APZC SEQ ID NO. 58 | 12 | 3 | 9 | 11 | 1 |
| K1-PtP | 5'-CPTPC SEQ ID NO. 59 3'-gZAZg SEQ ID NO. 60 | 12 | 12 | 12 | | |

Additional experiments were run with the following sequences containing S and B.
5'-CATGTC TGA TCC TGC ACT GCT GBGCSC TTGA CTC TCG TAC CTG-3' SEQ ID NO. 61
3'-AG ACT AGG ACG TGA CGA CSCGBG AACT GAG AGC ATG GAC TCG SEQ ID NO. 62
Converts to Sac1 site if it obeys the B->A + S->T rule.
If B->G + S->G then the result is an Apa1 site.
If sequence converts to B->A + S->C (and, no strand preference). then it is a Ban2 site
5'-CATGTC TGA TCC TGC ACT GCT STTAAB TTGA CTC TCG TAC CTG-3' SEQ ID NO. 63
3'-AG ACT AGG ACG TGA CGA BAATTS AACT GAG AGC ATG GAC TCG SEQ ID NO. 64
Converts to Dra1 site if it obeys the B->A + S->T rule.

TABLE 7

Sequencing of converted S/B (implemented by isoC and isoG) inserts from DH5α

| Data Set Name | Target Sequence | # of good sequences | iC:iG to C:G | iC:iG to T:A | iG:iC to G:C | iG:iC to A:T |
|---|---|---|---|---|---|---|
| 2isoC | 5'-GGGCCCT SEQ ID NO. 65 3'-CCCgGGA SEQ ID NO. 66 | 12 | 2 possible | 3 7 deletions | | |
| isoCG | 5'-gGggCCCC SEQ ID NO. 67 3'-CCCCggGg SEQ ID NO. 67 | 16 | 0 | 16 | 0 | 16 |
| K1-isoGc | 5'-TGCg SEQ ID NO. 68 3'-ACGC SEQ ID NO. 69 | 12 | 0 | 10 2 deletions | 1 | 11 |
| K1-isoCg | 5'-TCgg SEQ ID NO. 70 3'-AgCC SEQ ID NO. 71 | 5 | 1 | 4 | 0 | 4 1 deletion |
| K1-isoGtg | 5'-CGtGC SEQ ID NO. 72 3'-gCaCg SEQ ID NO. 73 | 17 | | | 2 | 32 |

TABLE 8

Dm-2isoC-2 set.

```
                    130       140       150       160       170       180
        Ref   GCACTGCTGGGCCCTTGACTCTCGTACCTGAGCGGAAGAGCGCGCAACGCAATTAATG
SEQ ID NO. 74
```

```
K1-      5'-CGtGC              17                              2        32
isoGtg   SEQ ID NO. 72
         3'-gCaCg
         SEQ ID NO. 73
```

Dm-2isoC-2 set.

```
                    130       140       150       160       170       180
        Ref   GCACTGCTGGGCCCTTGACTCTCGTACCTGAGCGGAAGAGCGCGCAACGCAATTAATG
SEQ ID NO. 74

Dm-2isoC1     ............T-............................................
SEQ ID NO. 75

Dm-2isoC3     ............TT............................................
SEQ ID NO. 76

Dm-2isoC4     ........A.G..TC...........................................
SEQ ID NO. 77

Dm-2isoC6     ............TT............................................
SEQ ID NO. 78

Dm-2isoC7     ............T-............................................
SEQ ID NO. 79

Dm-2isoC8     ............T-............................................
SEQ ID NO. 80

Dm-2isoC11    ............T-............................................
SEQ ID NO. 81

Dm-2isoC12    ............T-....TGACTCTCGTA.............................
SEQ ID NO. 82

Dm-2isoC17    ............TT............................................
SEQ ID NO. 83

Dm-2isoC18    ............T-............................................
SEQ ID NO. 84

Dm-2isoC19    ............T-............................................
SEQ ID NO. 85

Dm-2isoC20    ........A.G..TC...........................................
SEQ ID NO. 86
```

TABLE 9

Dm-isoCG-2 set

```
150       160       170       180       190       200
        ref   CGGTTCAGGACATGTCTGATCCTGCACTGCTGGGGCCCCTTGACTCTCGTACCTGAGCGGAAGAGCG
SEQ ID NO. 87

Dm-isoCG1     ...........................A....T.................................
SEQ ID NO. 88

Dm-isoCG2     ...........................A....T.............-...................
SEQ ID NO. 89

Dm-isoCG3     ...........................A....T.................................
SEQ ID NO. 90

Dm-isoCG4     ...........................A....T.................................
SEQ ID NO. 91

Dm-isoCG5     ............A..............A....T.................................
SEQ ID NO. 92
```

TABLE 9-continued

Dm-isoCG-2 set

```
Dm-isoCG6   A.. ..A.AA.A.GA........C-.......A....T............................
SEQ ID NO. 93

Dm-isoCG7   .TTGCACAA.GGG.AGGATGT..........A....T............................
SEQ ID NO. 94

Dm-isoCG8   ....................................A....T............................
SEQ ID NO. 95

Dm-isoCG9   ....................................A....T............................
SEQ ID NO. 96

Dm-isoCG10  ....................................A....T............................
SEQ ID NO. 97

Dm-isoCG11  ....................................A....T............................
SEQ ID NO. 98

Dm-isoCG12  ....................................A....T............................
SEQ ID NO. 99

Dm-isoCG13  .........................-..........A....T............................
SEQ ID NO. 100

Dm-isoCG14  ....................................A....T............................
SEQ ID NO. 101

Dm-isoCG18  ...............T-....................A....T............................
SEQ ID NO. 102

Dm-isoCG20  ....................................A....T............................
SEQ ID NO. 103
```

TABLE 10

K1-isoGC set

```
         130       140       150       160       170       180
    Ref  TCGACCCGGTCGTCGGTTCAGGACATGTCAACTCCTGCGTGCGGCCTTGACTCTCG-TAC
SEQ ID NO. 104

K1-isoGC-1   ..........................................A-...................
SEQ ID NO. 105

K1-isoGC-2   ...........................................T...................
SEQ ID NO. 106

K1-isoGC-3   ..........................................AT...................
SEQ ID NO. 107

K1-isoGC-4   ..........................................AT...................
SEQ ID NO. 107

K1-isoGC-5   ..........................................AT...................
SEQ ID NO. 107

K1-isoGC-8   ...................T........................AT...................
SEQ ID NO. 108

K1-isoGC-9   ..........................................AT...................
SEQ ID NO. 107

K1-isoGC-10  ..........................................A-...................
SEQ ID NO. 105

K1-isoGC-13  ..............-.............................AT......A..........
SEQ ID NO. 109

K1-isoGC-15  .........................................A.AT...................
SEQ ID NO. 110
```

TABLE 10-continued

K1-isoGC set

```
K1-isoGC-16    .........................................A.AT.................
SEQ ID NO. 110

K1-isoGC-17    ..........................................AT.................
SEQ ID NO. 107
```

Sequences are clean in this area.

TABLE 11

K1-isoCg set

```
150         160       170       180       190       200
    ref     CATGTCAACTCCTGCGTCGGGCCTTGACTCTCG-TACCTGAGCGGAAGAGCGCGCAACGCAATTAAT
SEQ ID NO. 111

K1-isoCg4      ...................CA.............................................
SEQ ID NO. 112

K1-isoCg12     ...................TA.............................................
SEQ ID NO. 113

K1-isoCg13     ...................T-..............................................
SEQ ID NO. 114

K1-isoCg15     ...................TA.............................................
SEQ ID NO. 113

K1-isoCg17     ...................TA.............................................
SEQ ID NO. 116

K1-isoGtG4     ........................A.A........................................
SEQ ID NO. 116

K1-isoGtG5     .......................-....A.A....................................
SEQ ID NO. 117

K1-isoGtG6     ........................A.A........................................
SEQ ID NO. 116

K1-isoGtG7     ........................A.A........................................
SEQ ID NO. 116

K1-isoGtG8     ........................A.A........................................
SEQ ID NO. 116

K1-isoGtG9     ........................A.A........................................
SEQ ID NO. 116

K1-isoGtG10    ........................A.A........................................
SEQ ID NO. 116

K1-isoGtG11    ........................A.A........................................
SEQ ID NO. 116

K1-isoGtG12    ........................A.A........................................
SEQ ID NO. 116

K1-isoGtG14    ........................A.A.......................................-
.....
SEQ ID NO. 118

K1-isoGtG16    ........................A.A........................................
SEQ ID NO. 116

K1-isoGTG17    ........................A.A........................................
SEQ ID NO. 116

K1-isoGtG19    ........................A.A........................................
SEQ ID NO. 116

K1-isoGtG20    ....................................................................
SEQ ID NO. 115
```

Example 2

In vitro construction of a gene encoding kanamycin resistance using S:B conversion.

We illustrate the instant invention by performing a total synthesis of a gene encoding an aminoglycoside 3'-phosphotransferase that, if expressed in an *E. coli* cell, confers kanamycin resistance. The strategy is implemented using the pairing between the AEGIS nucleotide 2'-deoxy-5-methyl-isocytidine (trivially designated S) and the AEGIS nucleotide 2'-deoxy-isoguanosine (trivially designated B). The S:B pair forms orthogonally to the T:A and C:G pairs, increasing the information density of DNA. Then, after S:B pairs guide hybridization, the ability of B to form a minor tautomer is used to mismatch dTTP opposite template B in template-directed polymerization. After this initial mismatch, the misincorporated T directs the incorporation of dATP, resulting in a net conversion of the S:B pairs in the preliminary construct to T:A pairs in the final construct.

Fragments were designed by software (OligArch) which takes as input a target sequence for a desired long DNA (L-DNA) construct. It then fragments the target to deliver, as output, a set of DNA fragment sequences that includes components of an artificially expanded genetic information system (AEGIS). OligArch designs these fragments so that after they are annealed, the annealed fragments are extended by a DNA polymerase to fill in any gaps, the nicks in the resulting duplex are ligated, and the AEGIS pairs are replaced by standard pairs by conversion PCR. The last step allows the desired L-DNA construct to emerge with only standard bases.

This difference (or "spread") between the melting temperature of the "weakest wanted" and "strongest unwanted" pairings is an indicator of the success of an autonomous assembly; the larger the spread, the more likely the assembly will succeed. With just four natural nucleotides, the spread is low, and becomes lower as the number of fragments is increased. Accordingly, various practitioners recommend attempting self-assembly with no more than a dozen or so fragments, although ca. three dozen have been assembled inside of yeast cells.

In this example, S (2'-deoxy-5-methyl-isocytidine) and B (2'-deoxy-isoguanosine) as the AEGIS nucleotides; adding these gives a six-letter GACTSB DNA alphabet. This was an alternative to the AEGIS nucleotides 2-amino-8-(1'-β-D-2'-deoxyribofuranosyl)-imidazo[1,2-a]-1,3,5-triazin-4(8H)one (trivially named P) and 6-amino-5-nitro-3-(1'-β-D-2'-deoxyribofuranosyl)-2(1H)-pyridone (trivially named Z), which give a GACTZP six-letter DNA alphabet. This choice reflected simpler conversion rules, to be discussed elsewhere.

The actual sequences designed by OligArch and used in this project are shown in Table 13, with overlaps. These were prepared by automated DNA synthesis from six phosphoramidites (four standard, two AEGIS). They were then mixed in equal amounts, heated and cooled. The 3'-(four standard, two AEGIS). They were then mixed in equal amounts, heated and cooled. The 3'-fragments were then extended at 60° C. using Phusion DNA polymerase to give a nicked construct. The nicks were then sealed with ligase.

TABLE 13

The sequences and overlaps of the fragments designed by OligArch to allow the autonomous assembly of a gene encoding an aminoglycoside 3'-phosphotransferase that confers upon *E. coli* resistance to kanamycin, aligned above the gene that arises via conversion PCR. The AEGIS nucleotides, S and B, were placed in the overlap regions to guide self-assembly.

```
Forward                                                                   SEQ ID No. 119
Fragments:     CACCATGAGCCATATTCAACGGGAAACGTCGAGGCCGCGATTAAATTCCAACATGGASGCSGASTT
Reverse                                                                   SEQ ID No. 120
Fragments:                                                   CCTBCGBCTBAATATACCCATATTTA
AEGIS                                                                     SEQ ID No. 140
Construct:   1 CACCATGAGCCATATTCAACGGGAAACGTCGAGGCCGCGATTAAATTCCAACATGGASGCSGASTTATATGGGTATAAAT
Converted                                                                 SEQ ID No. 139
Construct:   1 CACCATGAGCCATATTCAACGGGAAACGTCGAGGCCGCGATTAAATTCCAACATGGATGCTGATTTATATGGGTATAAAT Forward                                                                   SEQ ID No. 121
Fragments:                  SGTCGGGCABTCGGTGCGACAATCTATCGCTTGTATGGGAAGCCCGASGCGCCBGAG
Reverse                     SEQ ID No. 120                                SEQ ID No. 122
Fragments:     CCCGAGCGCTATTBCAGCCCGTSAGS                                 TBCGCGGSCTCAACAAAGAC
AEGIS                                                                     SEQ ID No. 140
Construct:  81 GGGCTCGCGATAASGTCGGGCABTCGGTGCGACAATCTATCGCTTGTATGGGAAGCCCGASGCGCCBGAGTTGTTTCTG
Converted                                                                 SEQ ID No. 139
Construct:  81 GGGCTCGCGATAATGTCGGGCAATCAGGTGCGACAATCTATCGCTTGTATGGGAAGCCCGATGCGCCAGAGTTGTTTCTG Forward                                                                   SEQ ID No. 123
Fragments:                        SGCCAASGASGTSACAGATGAGATGGTCAGACTAAACTGGCTGACGGABTTTATGCCSCT
Reverse                     SEQ ID No. 122                                SEQ ID No. 124
Fragments:     TTTGTACCGTTTCCATCGCABCGGTTBCTBCAB                                 TSAAATACGCBGA
AEGIS                                                                     SEQ ID No. 140
Construct: 161 AAACATGGCAAAGGTAGCGTSGCCAASGASGTSACAGATGAGATGGTCAGACTAAACTGGCTGACGGABTTTATGCCSCT
Converted                                                                 SEQ ID No. 139
Construct: 161 AAACATGGCAAAGGTAGCGTTGCCAATGATGTTACAGATGAGATGGTCAGACTAAACTGGCTGACGGAATTTATGCCTCT Forward         SEQ ID No. 123                                            SEQ ID No. 125
Fragments:     SC                          SACSCCSGASGATGCATGGTTACTCACCACTGCGATCCCCGGBAAAACBGCBTT
Reverse                     SEQ ID No. 124                                SEQ ID No. 126
Fragments:     BGGCTGGTAGTTCGTAAAATAGGCBTGBGGGBCTBCT                             CSTTTTGSCGSAAGG
AEGIS                                                                     SEQ ID No. 140
Construct: 241 SCCGACCATCAAGCATTTTATCCGSACSCCSGASGATGCATGGTTACTCACCACTGCGATCCCCGGBAAAACBGCBTTCC
Converted                                                                 SEQ ID No. 139
Construct: 241 TCCGACCATCAAGCATTTTATCCGTACTCCTGATGATGCATGGTTACTCACCACTGCGATCCCCGGAAAAACAGCATTCC
```

TABLE 13-continued

The sequences and overlaps of the fragments designed by OligArch to allow the
autonomous assembly of a gene encoding an aminoglycoside 3'-phosphotransferase that confers
upon E. coli resistance to kanamycin, aligned above the gene that arises via conversion PCR. The
AEGIS nucleotides, S and B, were placed in the overlap regions to guide self-assembly.

```
Forward                                                                    SEQ ID No. 127
Fragments:                          SGABAASATTGTSGATGCGCTGGCAGTGTTCCTGCGCCGGTTGCASTCGATT
Reverse                 SEQ ID No. 126                                     SEQ ID No. 128
Fragments:   TCCATAATCTTCTTATAGGACTAAGTCCBCTSTTBTAACABC                        TBAGCTAA
AEGIS                                                                      SEQ ID No. 140
Construct:321 AGGTATTAGAAGAATATCCTGATTCAGGSGABAASATTGTSGATGCGCTGGCAGTGTTCCTGCGCCGGTTGCASTCGATT
Converted                                                                  SEQ ID No. 139
Construct:321 AGGTATTAGAAGAATATCCTGATTCAGGTGAAAATATTGTTGATGCGCTGGCAGTGTTCCTGCGCCGGTTGCATTCGATT Forward      SEQ ID No. 127                                                SEQ ID No. 129
Fragments:   CCTGTST                      TCGSCTCGCSCAGGCGCAATCACGAATGAATAACGGTTGGT
Reverse                               SEQ ID No. 128                       SEQ ID No. 130
Fragments:   GGACABACATTAACAGGAAAATTGTCGCTAGCGCATAAAGCBGAGCGBG                 CBAACCA
AEGIS                                                                      SEQ ID No. 140
Construct:401 CCTGTSTGTAATTGTCCTTTTAACAGCGATCGCGTATTTCGSCTCGCSCAGGCGCAATCACGAATGAATAACGGTTGGT
Converted                                                                  SEQ ID No. 139
Construct:401 CCTGTTTGTAATTGTCCTTTTAACAGCGATCGCGTATTTCGTCTCGCTCAGGCGCAATCACGAATGAATAACGGTTTGGT Forward      SEQ ID No.129                                                 SEQ ID No. 131
Fragments:   SGASG                       SGTSGABCABGTCTGGAAAGAAATGCASAABCTSTTGCCBT
Reverse                               SEQ ID No. 130                       SEQ ID No. 132
Fragments:   BCTBCGCTCACTAAAACTACTGCTCGCATTACCGACCGGBCABCTSGTSC           TBTTSGABAACGGSA
AEGIS                                                                      SEQ ID No. 140
Construct:481 SGASGCGAGTGATTTTGATGACGAGCGTAATGGCTGGCCSGTSGABCABGTCTGGAAAGAAATGCASAABCTSTTGCCBT
Converted                                                                  SEQ ID No. 139
Construct:481 TGATGCGAGTGATTTTGATGACGAGCGTAATGGCTGGCCTGTTGAACAAGTCTGGAAAGAAATGCATAAACTTTTGCCAT Forward                                                                    SEQ ID No. 133
Fragments:                       ASTTCTCBCTSGASAACCTTATTTTTGACGAGGGGAAATTAATAGGTTGT
Reverse                 SEQ ID No. 132
Fragments:   AGAGTGGCCTAAGTCAGCAGTGAGTACCACTBAAGAGSGABCTB
AEGIS                                                                      SEQ ID No. 140
Construct:561 TCTCACCGGATTCAGTCGTCACTCATGGTGASTTCTCBCTSGASAACCTTATTTTTGACGAGGGGAAATTAATAGGTTGT
Converted                                                                  SEQ ID No. 139
Construct:561 TCTCACCGGATTCAGTCGTCACTCATGGTGATTTCTCACTTGATAACCTTATTTTTGACGAGGGGAAATTAATAGGTTGT Forward      SEQ ID No. 133                                                SEQ ID No. 135
Fragments:   ATTGASGTTGGACGBGT            BTACCAGGASCTSGCCATCCTATGGAACTGCCTCGGTGAGTTTTCTCC
Reverse                               SEQ ID No. 134                       SEQ ID No. 136
Fragments:   ACTBCAACCTGCSCAGCCTTAGCGTCTGGCSATGGTCCTBGABC                           G
AEGIS                                                                      SEQ ID No. 140
Construct:641 ATTGASGTTGGACGBGTCGGAATCGCAGACCGBTACCAGGASCTSGCCATCCTATGGAACTGCCTCGGTGAGTTTTCTCC
Converted                                                                  SEQ ID No. 139
Construct:641 ATTGATGTTGGACGAGTCGGAATCGCAGACCGATACCAGGATCTTGCCATCCTATGGAACTGCCTCGGTGAGTTTTCTCC Forward      SEQ ID No. 135                                                SEQ ID No. 137
Fragments:   STCBTTACAGAABC                          CSGASATGAASAABTTGCAGTTTCATTTGATGCTCG
Reverse                               SEQ ID No. 136
Fragments:   BAGSAATGTCTTSGCCGAAAAAGTTTTTATACCATAACTATTAGGBCTBTACTTBTTS
AEGIS                                                                      SEQ ID No. 140
Construct:721 STCBTTACAGAABCGGCTTTTTCAAAAATATGGTATTGATAATCCSGASATGAASAABTTGCAGTTTCATTTGATGCTCG
Converted                                                                  SEQ ID No. 139
Construct:721 TTCATTACAGAAACGGCTTTTTCAAAAATATGGTATTGATAATCCTGATATGAATAAATTGCAGTTTCATTTGATGCTCG Forward                    SEQ ID No. 137
Frag-         ATGAGTTTTTCTAACAGGATCCGCBCGBCSAG
ments:
Reverse                                                                    SEQ ID No. 138
Fragments:                          GCGSGCSGSTCGTCGACTGTCCTGCCTGSCTBGCSGGSGATC
AEGIS                                                                      SEQ ID No. 140
Con-     784  ATGAGTTTTTCTAACAGGATCCGCBCGBCSAGCAGCTGACAGGACGGACBGASCGBCCBCTAG
struct:
Converted                                                                  SEQ ID No. 139
Con-     784  ATGAGTTTTTCTAACAGGATCCGCACGACTAGCAGCTGACAGGACGGACAGATCGACCACTAG
struct:
```

The first indicator that indicated that the GACTSB AEGIS self-assembly was successful came before PCR. A gel resolving crude materials obtained from the "one pot" annealing, extension, and ligation process, without PCR amplification, showed a major band at ~863 base pairs, the size of the expected product. This suggested that the 20 fragments with AEGIS overhangs self-assembled to give the target gene as the principal product.

The product of the autonomous assembly was then ligated behind a beta-galactosidase promoter into a plasmid containing a gene conferring resistance of ampicillin. This was used to transform *E. coli* cells, which were found to grow in medium containing kanamycin. Plating experiments quantitated these results. Plates with kanamycin but no IPTG (which induces expression of the synthetic gene) gave no colonies. With IPTG, however, multiple colonies grew in the presence of kanamycin, with the expected smaller size than the colonies seen on plates lacking kanamycin altogether.

The final demonstration of the success of the GACTSB autonomous assembly came, of course, from the sequencing of the cloned product. Sequencing also allowed us to estimate the error associated with the process. While 1-2% errors were seen, errors were not found in the sites where S:B pairs had been present. Rather, the errors were found most frequently at the ends of the reads, as expected for sequencing errors, rather than errors in the primary synthesis, polymerase extension, or conversion PCR.

What is claimed is:

1. A process for constructing a DNA duplex, said process comprising (a) synthesizing a plurality of single stranded oligonucleotide fragments that comprise 5'-hybridizing regions, 3'-hybridizing regions and, optionally, regions between the 5'-hybridizing regions and 3'-hybridizing regions;

(b) contacting said oligonucleotide fragments and end fragments under conditions where their 5'-hybridizing regions and 3'-hybridizing regions hybridize to form a concatamer;

(c) filling in gaps, if they exist, in the concatamer by incubating the concatamer with a DNA polymerase, polymerase buffer, polymerase cofactor and 2'-deoxynucleoside triphosphates, said DNA polymerase being unable to displace strands under conditions where it fills said gaps; and (d) converting the concatamer into a ligated duplex structure by incubating said concatamer with DNA ligase in the presence of ligase buffer and ligase cosubstrates and cofactors, wherein said 5'-hybridizing regions and 3'-hybridizing regions contain one or more nonstandard nucleobases selected from the group consisting of

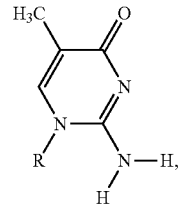
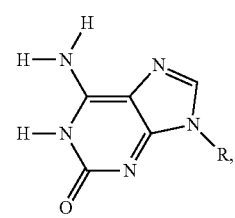
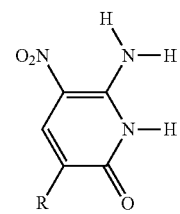
and
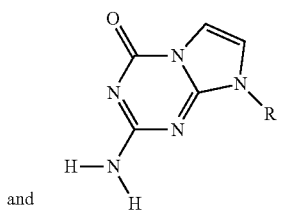

wherein R indicates the point of attachment of said nucleobase to said hybridizing regions.

2. The process of claim 1 wherein said non-standard nucleobases are selected from the group consisting of

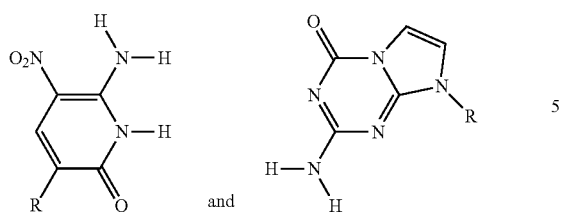

and wherein R indicates the point of attachment of said nucleobase to said hybridizing regions.

3. The process of claim 1 wherein said non-standard nucleobases are selected from the group consisting of

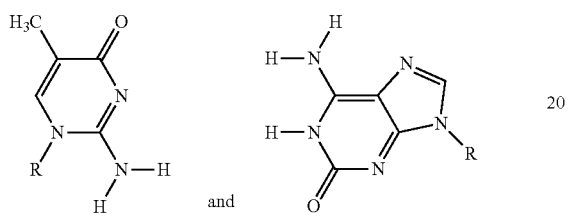

and wherein R indicates the point of attachment of said nucleobase to said hybridizing regions.

4. The process of claim 1, wherein said process is followed by a step wherein said non-standard nucleobases are converted to standard nucleobases.

* * * * *